United States Patent
Harrison et al.

(10) Patent No.: US 11,149,057 B2
(45) Date of Patent: Oct. 19, 2021

(54) NEUROACTIVE STEROIDS, COMPOSITIONS, AND USES THEREOF

(71) Applicant: Sage Therapeutics, Inc., Cambridge, MA (US)

(72) Inventors: Boyd L. Harrison, Princeton Junction, NJ (US); Gabriel Martinez Botella, Wayland, MA (US); Albert Jean Robichaud, Boston, MA (US); Francesco G. Salituro, Marlborough, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/924,814

(22) Filed: Jul. 9, 2020

(65) Prior Publication Data
US 2021/0094981 A1    Apr. 1, 2021

Related U.S. Application Data

(62) Division of application No. 16/269,779, filed on Feb. 7, 2019, now Pat. No. 10,745,436, which is a division of application No. 15/319,503, filed as application No. PCT/US2015/036500 on Jun. 18, 2015, now Pat. No. 10,246,482.

(60) Provisional application No. 62/014,010, filed on Jun. 18, 2014.

(51) Int. Cl.
| | |
|---|---|
| *C07J 41/00* | (2006.01) |
| *C07J 5/00* | (2006.01) |
| *C07J 7/00* | (2006.01) |
| *C07J 17/00* | (2006.01) |
| *C07J 1/00* | (2006.01) |
| *C07J 13/00* | (2006.01) |
| *C07J 21/00* | (2006.01) |

(52) U.S. Cl.
CPC .......... *C07J 41/005* (2013.01); *C07J 5/0015* (2013.01); *C07J 7/002* (2013.01); *C07J 7/009* (2013.01); *C07J 17/00* (2013.01); *C07J 1/0011* (2013.01); *C07J 7/007* (2013.01); *C07J 7/0085* (2013.01); *C07J 13/007* (2013.01); *C07J 21/00* (2013.01); *C07J 21/006* (2013.01); *C07J 21/008* (2013.01)

(58) Field of Classification Search
CPC .......... C07J 41/005; C07J 5/0015; C07J 7/002
See application file for complete search history.

(56) References Cited

U.S. PATENT DOCUMENTS

| | | | | |
|---|---|---|---|---|
| 4,071,625 A | * | 1/1978 | Grunwell | ................. C07J 17/00 514/172 |
| 9,365,611 B2 | * | 6/2016 | Martinez Botella | .... A61P 25/26 |

* cited by examiner

*Primary Examiner* — Pancham Bakshi
(74) *Attorney, Agent, or Firm* — Honigman LLP; Kathryn D. Doyle; Jonathan P. O'Brien

(57) ABSTRACT

Described herein are steroids of Formula (I):

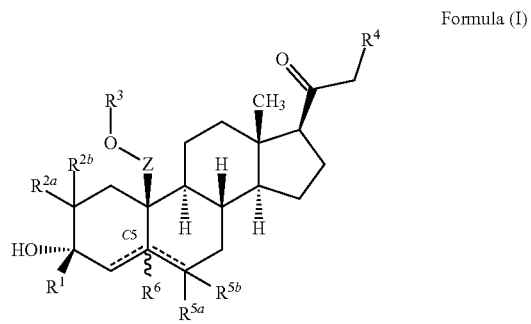

and pharmaceutically acceptable salts thereof; wherein $R^1$, $R^{2a}$, $R^{2b}$, $R^3$, $R^4$, $R^{5a}$, $R^{5b}$, $R^6$ and Z are as defined herein. Such compounds are contemplated useful for the prevention and treatment of a variety of CNS-related conditions, for example, treatment of sleep disorders, mood disorders, schizophrenia spectrum disorders, convulsive disorders, disorders of memory and/or cognition, movement disorders, personality disorders, autism spectrum disorders, pain, traumatic brain injury, vascular diseases, substance abuse disorders and/or withdrawal syndromes, and tinnitus.

33 Claims, No Drawings

NEUROACTIVE STEROIDS, COMPOSITIONS, AND USES THEREOF

RELATED APPLICATIONS

This Application is a Divisional of Ser. No. 16/269,779, filed Feb. 7, 2019, which is a Divisional of Ser. No. 15/319,503, filed Dec. 16, 2016, which is a National Stage Application under 35 U.S.C. § 371 of International Application No. PCT/US2015/036500, filed Jun. 18, 2015, published as International Publication No. WO2015/195962 on Dec. 23, 2015, which claims priority under 35 U.S.C. § 119(e) to U.S. Provisional Application No. 62/014,010 filed Jun. 18, 2014, the entire contents of which are incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids (Lan, N. C. et al., *Neurochem. Res.* 16:347-356 (1991)).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet*, 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy*, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium*, Raven Press, New York (1984), pp. 279-282, and Dalton, K.,

*Premenstrual Syndrome and Progesterone Therapy,* 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Provided herein are 19-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

In one aspect, the present invention provides compounds of Formula (I):

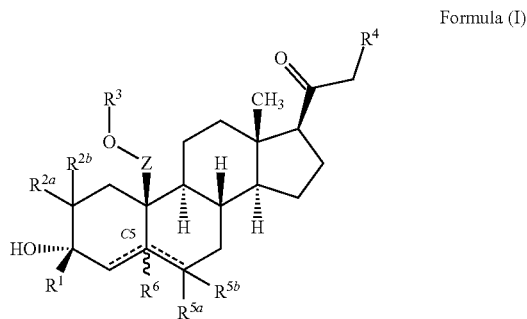

Formula (I)

or a pharmaceutically acceptable salt thereof, wherein: $R^1$ is $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —$OR^A$, or —$NR^BR^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); $R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, or —C(O)N$R^DR^C$; $R^4$ is hydrogen, $C_1$-$C_6$ alkyl, $C_2$-$C_6$ alkenyl, $C_2$-$C_6$ alkynyl, carbocyclyl, or —$OR^A$; ==== represents a single or double bond, wherein when one ==== is a double bond, the other ==== is a single bond; wherein when the ==== between $CR^6$ and $CR^{5a}R^{5b}$ is a double bond, then one of $R^{5a}$ or $R^{5b}$ is absent; and when one of the ==== is a double bond, $R^6$ is absent; Z is —$CR^{7a}R^{7b}$—, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring (e.g., carbocyclyl or heterocyclyl); each of $R^{5a}$ and $R^{5b}$ is independently absent, hydrogen, $C_1$-$C_6$ alkyl, or halo; $R^6$ is absent or hydrogen; $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); or $R^D$ is hydrogen, $C_1$-$C_6$ alkyl, carbocyclyl, heterocyclyl, aryl, or heteroaryl.

In one aspect, the present invention provides pharmaceutical compositions comprising a compound described herein, e.g., a compound of Formula (I), or pharmaceutically acceptable salt thereof, and a pharmaceutically acceptable excipient.

In one aspect, the present invention provides a method for treating a CNS-related disorder in a subject in need thereof, comprising administering to the subject an effective amount of a compound described herein, e.g., a compound of Formula (I), or a pharmaceutically acceptable salt thereof. In some embodiments, the CNS-related disorder is a sleep disorder, a mood disorder, a schizophrenia spectrum disorder, a convulsive disorder, a disorder of memory and/or cognition, a movement disorder, a personality disorder, a sleep disorder, autism spectrum disorder, pain, seizure, status epilepticus, depression (e.g., postnatal depression, postpartum depression), traumatic brain injury, a vascular disease, a substance abuse disorder and/or withdrawal syndrome, or tinnitus. In some embodiments, the compound is administered orally, subcutaneously, intravenously, or intramuscularly. In some embodiments, the compound is administered chronically.

In one aspect, the present invention provides a method for inducing anesthesia or sedation, comprising administering to the subject an effective amount of a compound described herein, e.g., a compound of Formula (I), or a pharmaceutically acceptable salt thereof.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—CH(CH$_3$)—, (—C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("C$_{2-20}$ alkenyl"). In certain embodiments, alkenyl does not contain any triple bonds. In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_2$ alkenyl"). In some embodiments, an alkenyl group has 2 to 5 carbon atoms ("C$_{2-5}$ alkenyl"). In some embodiments, an alkenyl group has 2 to 4 carbon atoms ("C$_2$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_2$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_9$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted C$_{2-10}$ alkenyl. In certain embodiments, the alkenyl group is substituted C$_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethylene (—C(CH$_3$)=CH—, —CH=C(CH$_3$)—), substituted propylene (e.g., —C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("C$_{2-20}$ alkynyl"). In certain embodiments, alkynyl does not contain any double bonds. In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_2$ alkynyl"). In some embodiments, an alkynyl group has 2 to 5 carbon atoms ("C$_{2-5}$ alkynyl"). In some embodiments, an alkynyl group has 2 to 4 carbon atoms ("C$_2$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_2$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkynyl groups include the aforementioned C$_2$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted C$_{2-10}$ alkynyl. In certain embodiments, the alkynyl group is substituted C$_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and for 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and for 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and for 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

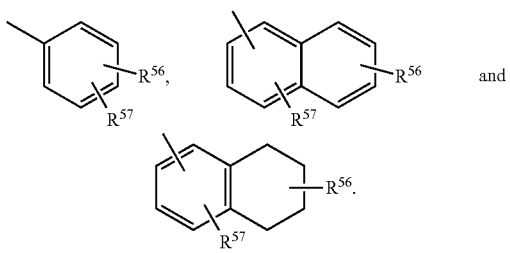

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

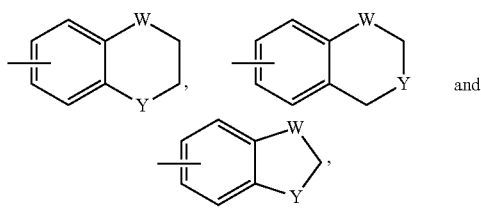

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5membered heteroaryl groups containing one heteroatom include, without limitation, pyrrolyl, furanyl and thiophenyl. Exemplary 5membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

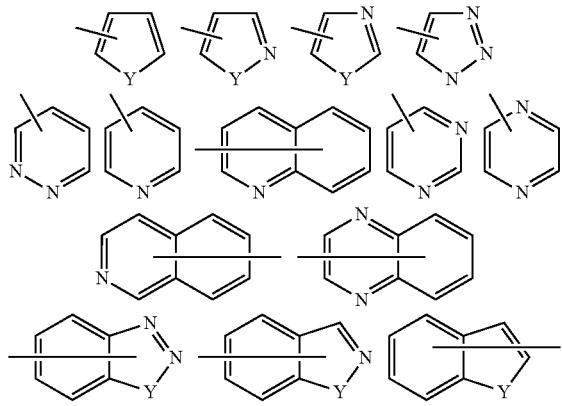

wherein each Y is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$, octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_5$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10 membered nonaromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxepanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

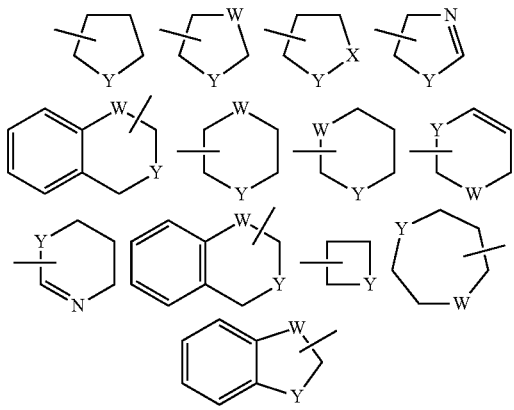

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, C(O)—(CH$_2$)$_t$(C$_6$-C$_{10}$ aryl), C(O)—(CH$_2$)$_t$(5-10 membered heteroaryl), —C(O)—(CH$_2$)$_t$(C$_3$-C10 cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}$C(O)$R^{23}$, where each instance of $R^{22}$ and $R^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}$C(O)— $C_1$-$C_8$ alkyl, —$NR^{24}$C(O)—(CH$_2$)$_t$(C$_6$-$C_{10}$ aryl), —$NR^{24}$C (O)—(CH$_2$)$_t$(5-10 membered heteroaryl), —$NR^{24}$C(O)— (CH$_2$)$_t$(C$_3$-$C_{10}$ cycloalkyl), and —$NR^{24}$C(O)—(CH$_2$)$_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, $NR^{39}$—$C_1$-$C_8$ alkyl, —$NR^{39}$—(CH$_2$)$_t$($C_6$-C10 aryl), —$NR^{39}$—(CH$_2$)$_t$(5-10 membered heteroaryl), —$NR^{39}$—(CH$_2$)$_t$($C_3$-$C_{10}$ cycloalkyl), and —$NR^{39}$—(CH$_2$)$_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, C(O)$NR^{64}$—$C_1$-$C_8$ alkyl, C(O)$NR^{64}$—(CH$_2$)$_t$($C_6$-$C_{10}$ aryl), C(O)$N^{64}$—(CH$_2$)$_t$(5-10 membered heteroaryl), C(O)$NR^{64}$—(CH$_2$)$_t$($C_3$-$C_{10}$ cycloalkyl), and C(O)$NR^{64}$—(CH$_2$)$_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethylene" refers to substituted or unsubstituted —(C—C)—.

"Ethenyl" refers to substituted or unsubstituted —(C=C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C(O$R^{cc}$)$_2$, —$CO_2R^{aa}$, —OC(=O)$R^{aa}$, —$OCO_2R^{aa}$, —C(=O)$N(R^{bb})_2$, —OC(=O)$N(R^{bb})_2$, —$NR^{bb}$C(=O)$R^{aa}$, —$NR^{bb}CO_2R^{aa}$, —$NR^{bb}$C(=O)$N(R^{bb})_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)$N(R^{bb})_2$, —OC(=$NR^{bb}$)$N(R^{bb})_2$, —$NR^{bb}$C(=$NR^{bb}$)$N(R^{bb})_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(O)$R^{aa}$, e.g., —S(=O)$R^{aa}$, —OS(=O)$R^{aa}$, —Si($R^{aa}$)$_3$, —OSi($R^{aa}$)$_3$ —C(=S)$N(R^{bb})_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)(O$R^{cc}$)$_2$, —P(=O)$_2N(R^{bb})_2$, —OP(=O)$_2N(R^{bb})_2$, —P(=O)($NR^{bb}$)$_2$, —OP(=O)($NR^{bb}$)$_2$, —$NR^{bb}$P(=O)(O$R^{cc}$)$_2$, —$NR^{bb}$P(=O)($NR^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —$BR^{aa}$(O$R^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2N(R^{cc})_2$, —P(=O)($NR^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rad groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rad groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(O)R$^{ee}$, e.g., —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O) (OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$,—SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP (=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, SO$_4$$^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides C19-substituted neuroactive steroids designed, for example, to act as GABA modulators. In certain embodiments, such compounds are envisioned to be useful as therapeutic agents for the inducement of anesthesia and/or sedation in a subject. In certain embodiments, such compounds are envisioned to be useful as therapeutic agents for treating a CNS-related disorder.

Compounds

In one aspect, provided herein are compounds according to Formula (I):

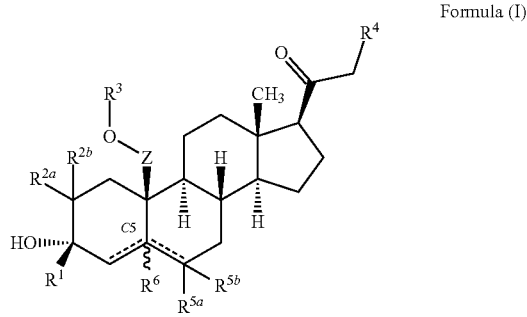

Formula (I)

or a pharmaceutically acceptable salt thereof, wherein: $R^1$ is $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —$OR^A$, or —$NR^BR^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); $R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, or —$C(O)NR^BR^C$; $R^4$ is hydrogen, $C_1$-$C_6$ alkyl, $C_2$-$C_6$ alkenyl, $C_2$-$C_6$ alkynyl, carbocyclyl, or —$OR^A$; ==== represents a single or double bond, wherein when one ==== is a double bond, the other ==== is a single bond; wherein when the ==== between —$CR^6$ and —$CR^{5a}R^{5b}$ is a double bond, then one of $R^{5a}$ or $R^{5b}$ is absent; and when one of the is a double bond, $R^6$ is absent; each of $R^{5a}$ and $R^{5b}$ is independently absent, hydrogen, $C_1$-$C_6$ alkyl, or halo; $R^6$ is absent or hydrogen; Z is —$CR^{7a}R^{7b}$, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring (e.g., carbocyclyl or heterocyclyl); $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); or $R^D$ is hydrogen, $C_1$-$C_6$ alkyl, carbocyclyl, heterocyclyl, aryl, or heteroaryl.

In certain embodiments, $R^1$ is $C_2$-$C_6$ alkyl, $C_2$-$C_6$ alkenyl, $C_2$-$C_6$ alkynyl, carbocyclyl, or heterocyclyl. In certain embodiments, $R^1$ is $C_1$-$C_6$ alkyl. In certain embodiments, $R^1$ is methyl.

In certain embodiments, $R^{2a}$ or $R^{2b}$ is hydrogen. In certain embodiments, both $R^{2a}$ and $R^{2b}$ are hydrogen.

In certain embodiments, $R^1$ is $C_1$-$C_6$ alkyl and both $R^{2a}$ and $R^{2b}$ are hydrogen. In certain embodiments, $R^1$ is methyl and $R^{2a}$ or $R^{2b}$ is hydrogen. In certain embodiments, $R^1$ is methyl and both $R^{2a}$ and $R^{2b}$ are hydrogen.

In certain embodiments, $R^3$ is $C_2$-$C_6$ alkyl, $C_2$-$C_6$ alkenyl, $C_2$-$C_6$ alkynyl, carbocyclyl, heterocyclyl, $C(O)R^A$, —C(O)OR$^A$, —C(O)NR$^B$R$^C$, or —S(O)$_x$R$^D$. In certain embodiments, $R^3$ is $C_1$-$C_6$ alkyl, carbocyclyl, heterocyclyl, or —C(O)NR$^B$R$^C$. In certain embodiments, $R^3$ is $C_1$-$C_6$ alkyl, for example, methyl, ethyl, or propyl.

In certain embodiments, $R^1$ is methyl and $R^3$ is $C_1$-$C_6$ alkyl, for example, methyl, ethyl, or propyl.

In certain embodiments, $R^3$ is heterocyclyl, for example, tetrahydropyranyl.

In certain embodiments, $R^1$ is methyl and $R^3$ is heterocyclyl, for example, tetrahydropyranyl.

In certain embodiments, $R^3$ is C(O)NR$^B$R$^C$, for example, C(O)NHCH$_2$CH$_3$.

In certain embodiments, $R^1$ is methyl and $R^3$ is C(O)NR$^B$R$^C$, for example, C(O)NHCH$_2$CH$_3$.

In certain embodiments, $R^4$ is $C_1$-$C_6$ alkyl, $C_2$-$C_6$ alkenyl, $C_2$-$C_6$ alkynyl, or carbocyclyl. In certain embodiments, $R^4$ is —OR$^A$ and $R^A$ is $C_1$-$C_6$ alkyl. In certain embodiments, $R^4$ is hydrogen, $C_1$-$C_6$ alkyl, or —OH. In certain embodiments, $R^4$ is —OH. In certain embodiments, $R^4$ is hydrogen.

In certain embodiments, the ==== between —CR$^6$ and —CR$^{5a}$R$^{5b}$ is a single bond, and $R^{5a}$ or $R^{5b}$ is hydrogen.

In certain embodiments, $R^1$ is methyl, the ==== between —CR$^6$ and —CR$^{5a}$R$^{5b}$ is a single bond, and $R^{5a}$ or $R^{5b}$ is hydrogen.

In certain embodiments, the ==== between —CR$^6$ and —CR$^{5a}$R$^{5b}$ is a single bond, and both $R^{5a}$ and $R^{5b}$ are hydrogen.

In certain embodiments, $R^1$ is methyl, the ==== between —CR$^6$ and —CR$^{5a}$R$^{5b}$ is a single bond, and both $R^{5a}$ and $R^{5b}$ are hydrogen.

In certain embodiments, both $R^{2a}$ and $R^{2b}$ are hydrogen, the ==== between —CR$^6$ and —CR$^{5a}$R$^{5b}$ is a single bond, and $R^{5a}$ or $R^{5b}$ is hydrogen. In certain embodiments, both $R^{2a}$ and $R^{2b}$ are hydrogen, the ==== between —CR$^6$ and —CR$^{5a}$R$^{5b}$ is a single bond, and both $R^{5a}$ and $R^{5b}$ are hydrogen.

In certain embodiments, $R^4$ is $C_1$-$C_6$ alkyl or —OR$^A$, the ==== between —CR$^6$ and —CR$^{5a}$R$^{5b}$ is a single bond, and $R^{5a}$ or $R^{5b}$ is hydrogen. In certain embodiments, $R^4$ is $C_1$-$C_6$ alkyl or —OR$^A$, the ==== between —CR$^6$ and —CR$^{5a}$R$^{5b}$ is a single bond, and both $R^{5a}$ and $R^{5b}$ are hydrogen.

In certain embodiments, the ==== between —CR$^6$ and —CR$^{5a}$R$^{5b}$ is a double bond, one of $R^{5a}$ or $R^{5b}$ is hydrogen, and the other of $R^{5a}$ or $R^{5b}$ is absent.

In certain embodiments, Z is $R^{7a}$ is hydrogen. In certain embodiments, Z is $R^{7b}$ is hydrogen. In certain embodiments, Z is $R^{7a}$ is $C_1$-$C_6$ alkyl. In certain embodiments, Z is $R^{7b}$ is $C_1$-$C_6$ alkyl. In certain embodiments, Z is $R^{7a}$ is hydrogen and $R^{7b}$ is $C_1$-$C_6$ alkyl. In certain embodiments, Z is $R^{7b}$ is —CH$_3$.

In certain embodiments, Z is —CH$_2$—.

In certain embodiments, the compound of Formula (I) is a compound of Formula (Ia):

Formula (Ia)

or a pharmaceutically acceptable salt thereof, wherein $R^1$ is $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —OR$^A$, or —NR$^B$R$^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); $R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)R$^A$, —C(O)OR$^A$, or —C(O)NR$^B$R$^C$; $R^4$ is hydrogen, $C_1$-$C_6$ alkyl, $C_2$-$C_6$ alkenyl, $C_2$-$C_6$ alkynyl, carbocyclyl, or OR$^A$; each of $R^{5a}$ and $R^{5b}$ is independently absent, hydrogen, $C_1$-$C_6$ alkyl, or halo; Z is —CR$^{7a}$R$^{7b}$, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring (e.g., carbocyclyl or heterocyclyl); $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); or $R^D$ is hydrogen, $C_1$-$C_6$ alkyl, carbocyclyl, aryl, or heteroaryl.

In certain embodiments, $R^1$ is $C_2$-$C_6$ alkyl, $C_2$-$C_6$ alkenyl, $C_2$-$C_6$ alkynyl, carbocyclyl, or heterocyclyl. In certain embodiments, $R^1$ is $C_1$-$C_6$ alkyl. In certain embodiments, $R^1$ is methyl.

In certain embodiments, $R^{2a}$ or $R^{2b}$ is hydrogen. In certain embodiments, both $R^{2a}$ and $R^{2b}$ are hydrogen.

In certain embodiments, $R^1$ is $C_1$-$C_6$ alkyl and both $R^{2a}$ and $R^{2b}$ are hydrogen. In certain embodiments, $R^1$ is methyl and $R^{2a}$ or $R^{2b}$ is hydrogen. In certain embodiments, $R^1$ is methyl and both $R^{2a}$ and $R^{2b}$ are hydrogen.

In certain embodiments, $R^3$ is $C_2$-$C_6$ alkyl, $C_2$-$C_6$ alkenyl, $C_2$-$C_6$ alkynyl, carbocyclyl, heterocyclyl, —C(O)R$^A$, —C(O)OR$^A$, —C(O)NR$^B$R$^C$, or —S(O)$_x$R$^D$. In certain embodiments, $R^3$ is $C_1$-$C_6$ alkyl, carbocyclyl, heterocyclyl, or —C(O)NR$^B$R$^C$. In certain embodiments, $R^3$ is $C_1$-$C_6$ alkyl, for example, methyl, ethyl, or propyl.

In certain embodiments, $R^1$ is methyl and $R^3$ is $C_1$-$C_6$ alkyl, for example, methyl, ethyl, or propyl.

In certain embodiments, $R^4$ is $C_1$-$C_6$ alkyl, $C_2$-$C_6$ alkenyl, $C_2$-$C_6$ alkynyl, or carbocyclyl. In certain embodiments, $R^4$ is hydrogen, $C_1$-$C_6$ alkyl, or —OH. In certain embodiments, $R^4$ is hydrogen.

In certain embodiments, $R^{5a}$ or $R^{5b}$ is hydrogen.

In certain embodiments, $R^1$ is methyl and $R^{5a}$ or $R^{5b}$ is hydrogen.

In certain embodiments, both $R^{5a}$ and $R^{5b}$ are hydrogen.

In certain embodiments, $R^1$ is methyl and both $R^{5a}$ and $R^{5b}$ are hydrogen.

In certain embodiments, both $R^{2a}$ and $R^{2b}$ are hydrogen and $R^{5a}$ or $R^{5b}$ is hydrogen. In certain embodiments, both $R^{2a}$ and $R^{2b}$ are hydrogen and both $R^{5a}$ and $R^{5b}$ are hydrogen.

In certain embodiments, $R^4$ is $C_1$-$C_6$ alkyl and $R^{5a}$ or $R^{5b}$ is hydrogen. In certain embodiments, $R^4$ is $C_1$-$C_6$ alkyl and both $R^{5a}$ and $R^{5b}$ are hydrogen.

In certain embodiments, the compound of Formula (Ia) is selected from:

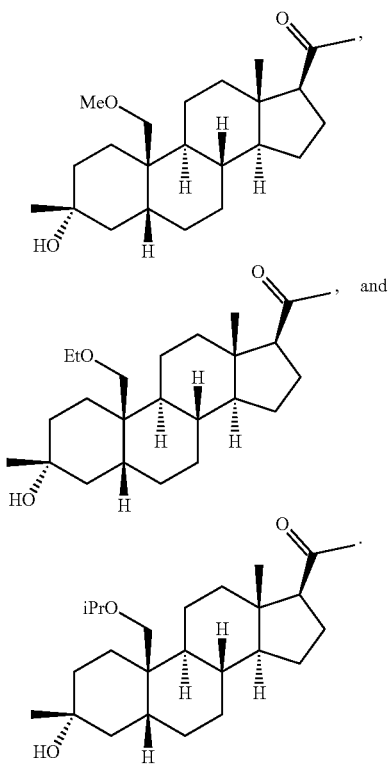

In certain embodiments, the compound of Formula (I) is a compound of Formula (Ib):

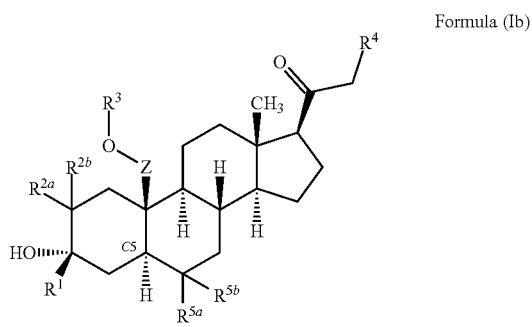

Formula (Ib)

or a pharmaceutically acceptable salt thereof, wherein $R^1$ is $C_1$-$C_6$ alkyl, $C_2$-$C_6$ alkenyl, $C_2$-$C_6$ alkynyl, carbocyclyl, or heterocyclyl; each of $R^{2a}$ and $R^{2b}$ is independently hydrogen, $C_1$-$C_6$ alkyl, halo, cyano, —$OR^A$, or —$NR^BR^C$, or $R^{2a}$ and $R^{2b}$ together with the carbon atom to which they are attached form a ring (e.g., a 3-7-membered ring, e.g., a 5-7-membered ring; a ring containing at least one heteroatom, e.g., a nitrogen, oxygen, or sulfur atom); $R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, or —$C(O)NR^DR^C$; $R^4$ is hydrogen, $C_1$-$C_6$ alkyl, $C_2$-$C_6$ alkenyl, $C_2$-$C_6$ alkynyl, carbocyclyl, or $OR^A$; each of $R^{5a}$ and $R^{5b}$ is independently absent, hydrogen, $C_1$-$C_6$ alkyl, or halo; Z is —$CR^{7a}R^{7b}$, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring (e.g., carbocyclyl or heterocyclyl); $R^A$ is hydrogen, $C_1$-$C_6$ alkyl, carbocyclyl, heterocyclyl, aryl, or heteroaryl; each of $R^B$ and $R^C$ is independently hydrogen, $C_1$-$C_6$ alkyl, carbocyclyl, heterocyclyl, aryl, heteroaryl, or taken together with the atom to which they are attached form a ring (e.g., a 3-7-membered ring, e.g., a 5-7-membered ring; a ring containing at least one heteroatom, e.g., a nitrogen, oxygen, or sulfur atom); or $R^D$ is hydrogen, $C_1$-$C_6$ alkyl, carbocyclyl, heterocyclyl, aryl, or heteroaryl.

In certain embodiments, $R^1$ is $C_2$-$C_6$ alkyl, $C_2$-$C_6$ alkenyl, $C_2$-$C_6$ alkynyl, carbocyclyl, or heterocyclyl. In certain embodiments, $R^1$ is $C_1$-$C_6$ alkyl. In certain embodiments, $R^1$ is methyl.

In certain embodiments, $R^{2a}$ or $R^{2b}$ is hydrogen. In certain embodiments, both $R^{2a}$ and $R^{2b}$ are hydrogen.

In certain embodiments, $R^1$ is $C_1$-$C_6$ alkyl and both $R^{2a}$ and $R^{2b}$ are hydrogen. In certain embodiments, $R^1$ is methyl and $R^{2a}$ or $R^{2b}$ is hydrogen. In certain embodiments, $R^1$ is methyl and both $R^{2a}$ and $R^{2b}$ are hydrogen.

In certain embodiments, $R^3$ is $C_2$-$C_6$ alkyl, $C_2$-$C_6$ alkenyl, $C_2$-$C_6$ alkynyl, carbocyclyl, heterocyclyl, —$C(O)R^A$, —$C(O)OR^A$, —$C(O)NR^BR^C$, or $S(O)R^D$. In certain embodiments, $R^3$ is $C_1$-$C_6$ alkyl, for example, methyl, ethyl, or propyl.

In certain embodiments, $R^1$ is methyl and $R^3$ is $C_1$-$C_6$ alkyl, for example, methyl, ethyl, or propyl.

In certain embodiments, $R^3$ is heterocyclyl, for example, tetrahydropyranyl.

In certain embodiments, $R^1$ is methyl and $R^3$ is heterocyclyl, for example, tetrahydropyranyl.

In certain embodiments, $R^3$ is $C(O)NR^BR^C$, for example, $C(O)NHCH_2CH_3$.

In certain embodiments, $R^1$ is methyl and $R^3$ is $C(O)NR^BR^C$, for example, $C(O)NHCH_2CH_3$.

In certain embodiments, $R^4$ is $C_1$-$C_6$ alkyl, $C_2$-$C_6$ alkenyl, $C_2$-$C_6$ alkynyl, or carbocyclyl. In certain embodiments, $R^4$ is hydrogen, $C_1$-$C_6$ alkyl, or hydroxyl. In certain embodiments, $R^4$ is —OH. In certain embodiments, $R^4$ is hydrogen.

In certain embodiments, $R^{54a}$ or $R^{5b}$ is hydrogen.

In certain embodiments, $R^1$ is methyl and $R^{5a}$ or $R^{5b}$ is hydrogen.

In certain embodiments, both $R^{5a}$ and $R^{5b}$ are hydrogen.

In certain embodiments, $R^1$ is methyl and both $R^{5a}$ and $R^{5b}$ are hydrogen.

In certain embodiments, both $R^{2a}$ and $R^{2b}$ are hydrogen and $R^{5a}$ or $R^{5b}$ is hydrogen. In certain embodiments, both $R^{2a}$ and $R^{2b}$ are hydrogen and both $R^{5a}$ and $R^{5b}$ are hydrogen.

In certain embodiments, $R^4$ is $C_1$-$C_6$ alkyl and $R^{5a}$ or $R^{5b}$ is hydrogen. In certain embodiments, $R^4$ is $C_1$-$C_6$ alkyl and both $R^{5a}$ and $R^{5b}$ are hydrogen.

In certain embodiments, the compound of Formula (Ib) is selected from:

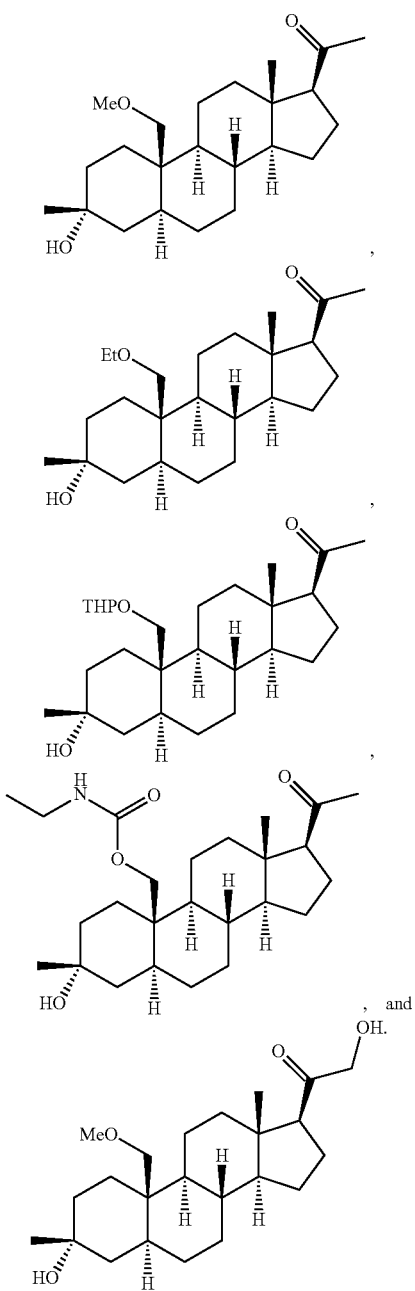

A pharmaceutical composition comprising a compound as described herein, e.g., a compound of Formula (I), or pharmaceutically acceptable salt thereof, and a pharmaceutically acceptable excipient.

A method for treating a CNS-related disorder in a subject in need thereof, comprising administering to the subject an effective amount of a compound as described herein, e.g., a compound of Formula (I), or pharmaceutically acceptable salt thereof. In certain embodiments, the CNS-related disorder is a sleep disorder, a mood disorder, a schizophrenia spectrum disorder, a convulsive disorder, a disorder of memory and/or cognition, a movement disorder, a personality disorder, a sleep disorder, autism spectrum disorder, pain, seizure, status epilepticus, depression (e.g., postnatal depression, postpartum depression), traumatic brain injury, a vascular disease, a substance abuse disorder and/or withdrawal syndrome, or tinnitus. In certain embodiments, the compound is administered orally, subcutaneously, intravenously, or intramuscularly. In certain embodiments, the compound is administered chronically.

A method for inducing anesthesia or sedation, comprising administering to the subject an effective amount of a compound as described herein, e.g., a compound of Formula (I), or pharmaceutically acceptable salt thereof.

Pharmaceutical Compositions

In another aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable formulations of a compound of the present invention. In one embodiment, the formulation comprises water. In another embodiment, the formulation comprises a cyclodextrin derivative. The most common cyclodextrins α-, β- and γ-cyclodextrins consisting of 6, 7 and 8 α-1,4linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin (e.g., 10-50% in water).

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of the present invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of the present invention may be admixed as a dry powder with a starch diluent in an approximate 1:1 weight ratio. The mixture is filled into 250 mg capsules (125 mg of active compound per capsule).

Exemplary Formulation 3—Liquid: A compound of the present invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of the present invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of the present invention may be dissolved or suspended in a buffered sterile saline injectable aqueous medium to a concentration of approximately 5 mg/mL.

Exemplary Formulation 6—Tablets: A compound of the present invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of the present invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of the present invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of the present invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of the present invention may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Methods of Use and Treatment

As generally described herein, the present invention is directed to C19-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Howell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neurodegenerative Diseases and Disorders

The compounds described herein can be used in a method described herein, for example in the treatment of a disorder described herein such as a neurodegenerative disease.

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

The compounds described herein can be used in a method described herein, for example in the treatment of a disorder described herein such as a mood disorder.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Premenstrual dysphoric disorder (PMDD) refers to a severe, at times disabling extension of premenstrual syndrome (PMS). PMDD causes extreme modd shifts with symptoms that typically begin seven to ten days before a female's period starts and continues for the first few days of a female's period. Symptoms include sadness or hopelessness, anxiety or tension, extreme moodiness, and marked irritability or anger.

Symptoms of depression include persistent anxious or sad feelings, feelings of helplessness, hopelessness, pessimism, worthlessness, low energy, restlessness, irritability, fatigue, loss of interest in pleasurable activities or hobbies, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

The compounds described herein can be used in a method described herein, for example in the treatment of a disorder described herein such as an anxiety disorder.

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Eating Disorders

The compounds described herein can be used in a method described herein, for example in the treatment of a disorder described herein such as an eating disorder. Eating disorders feature disturbances in eating behavior and weight regulation, and are associated with a wide range of adverse psychological, physical, and social consequences. An individual with an eating disorder may start out just eating smaller or larger amounts of food, but at some point, their urge to eat less or more spirals out of control. Eating disorders may be characterized by severe distress or concern about body weight or shape, or extreme efforts to manage weight or food intake. Eating disorders include anorexia nervosa, bulimia nervosa, binge-eating disorder, cachexia, and their variants.

Individuals with anorexia nervosa typically see themselves as overweight, even when they are underweight. Individuals with anorexia nervosa can become obsessed with eating, food, and weight control. Individuals with anorexia nervosa typically weigh themselves repeatedly, portion food carefully, and eat very small quantities of only certain foods. Individuals with anorexia nervosa may engage in binge eating, followed by extreme dieting, excessive exercise, self-induced vomiting, or misuse of laxatives, diuretics, or enemas. Symptoms include extremely low body weight, severe food restriction, relentless pursuit of thinness and unwillingness to maintain a normal or healthy weight, intense fear of gaining weight, distorted body image and self-esteem that is heavily influenced by perceptions of body weight and shape, or a denial of the seriousness of low body weight, lack of menstruation among girls and women. Other symptoms include the thinning of the bones, brittle hair and nails, dry and yellowish skin, growth of fine hair all over the body, mild anemia, muscle wasting, and weakness, severe constipation, low blood pressure or slowed breathing and pulse, damage to the structure and function of the heart, brain damage, multi-organ failure, drop in internal body temperature, lethargy, sluggishness, and infertility.

Individuals with bulimia nervosa have recurrent and frequent episodes of eating unusually large amounts of food and feel a lack of control over these episodes. This binge eating is followed by behavior that compensates for the overeating such as forced vomiting, excessive use of laxatives or diuretics, fasting, excessive exercise, or a combination of these behaviors.

Unlike anorexia nervosa, people with bulimia nervosa usually maintain what is considered a healthy or normal weight, while some are slightly overweight. But like people with anorexia nervosa, they typically fear gaining weight, want desperately to lose weight, and are unhappy with their body size and shape. Usually, bulimic behavior is done secretly because it is often accompanied by feelings of disgust or shame. The binge eating and purging cycle can happen anywhere from several times a week to many times a day. Other symptoms include chronically inflamed and sore throat, swollen salivary glands in the neck and jaw area, worn tooth enamel, and increasingly sensitive and decaying teeth as a result of exposure to stomach acid, acid reflux disorder and other gastrointestinal problems, intestinal distress and irritation from laxative abuse, severe dehydration from purging of fluids, electrolyte imbalance (that can lead to a heart attack or stroke).

Individuals with binge-eating disorder lose control over their eating. Unlike bulimia nervosa, periods of binge eating are not followed by compensatory behaviors like purging, excessive exercise, or fasting. Individuals with binge-eating disorder often are overweight or obese. Obese individuals with binge-eating disorder are at higher risk for developing cardiovascular disease and high blood pressure. They also experience guilt, shame, and distress about their binge eating, which can lead to more binge eating.

Cachexia is also known as "wasting disorder," and is an eating-related issue experienced by many cancer patients. Individuals with cachexia may continue to eat normally, but their body may refuse to utilize the vitamins and nutrients that it is ingesting, or they will lose their appetite and stop eating. When an individual experiences loss of appetite and stops eating, they can be considered to have developed anorexia nervosa.

Epilepsy

The compounds described herein can be used in a method described herein, for example in the treatment of a disorder described herein such as epilepsy, status epilepticus, or seizure, for example as described in WO2013/112,605 and WO/2014/031,792, the contents of which are incorporated herein in their entirety.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

Tremor

The compounds described herein can be used in a method described herein, for example in the treatment of a disorder described herein such as tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity.

Orthostatic tremor is characterized by fast (e.g., greater than 12 Hz) rhythmic muscle contractions that occurs in the legs and trunk immediately after standing Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Anesthesia/Sedation

The compounds described herein can be used in a method described herein, for example to induce anesthesia or sedation. Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, N.Y., 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

¹H-NMR reported herein (e.g., for intermediates) may be a partial representation of the full NMR spectrum of a compound, e.g., a compound described herein.

Exemplary general method for preparative HPLC: Column: Waters RBridge prep 10 □m C18, 19*250 mm. Mobile phase: aectonitrile, water (NH₄HCO₃) (30 L water, 24 g NH₄HCO₃, 30 mL NH₃·H₂O). Flow rate: 25 mL/min Exemplary general method for analytical HPLC: Mobile phase: A: water (10 mM NH₄HCO₃), B: acetonitrile Gradient: 5%-95% B in 1.6 or 2 min Flow rate: 1.8 or 2 mL/min; Column: XBridge C18, 4.6*50 mm, 3.5 μm at 45° C.

Synthetic Procedures

Example 1. General Procedure A: Preparation of Compound 1

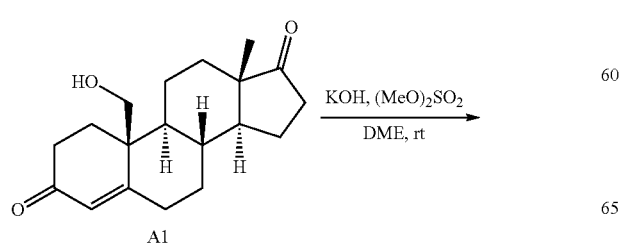

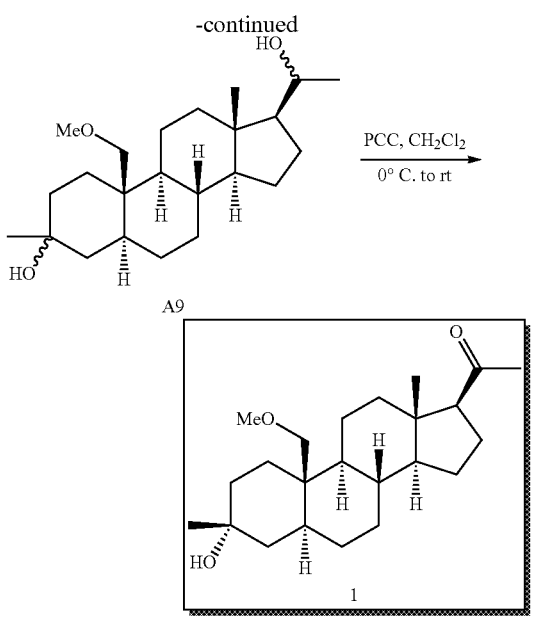

Step 1. Preparation of compound A2. Finely-ground potassium hydroxide (28.0 g, 165 mmol) was added to a solution of commercially available 19-hydroxyandrost-4-ene-3,17-dione (A1, 50.0 g, 165 mmol) in anhydrous 1,2-dimethoxyethane (500 mL) at 0° C. under nitrogen, after which methyl sulfate (43.7 g, 208 mmol) was added portionwise. The mixture was slowly warmed to room temperature, stirring for a total of 18 h, at which point TLC analysis of the mixture (7:3 hexanes/ethyl acetate) indicated completion of the reaction. The mixture was diluted with water (500 mL) and extracted with ethyl acetate (3×200 mL). The combined organic extracts were washed with saturated aqueous sodium chloride solution (100 mL), dried with anhydrous sodium sulfate and filtered. The solvents were removed under reduced pressure and the residue was purified by column chromatography on silica gel, eluting with heptane/ethyl acetate (2:1), to provide A2 as a yellow solid (26.8 g, 50%).

Step 2. Preparation of compound A3. Triethyl orthoformate (6.2 mL, 37 mmol) and p-toluenesulfonic acid (400 mg, 9.3 mmol) were added to a solution of compound A2 (9.9 g, 31.0 mmol) in anhydrous 1,4-dioxane (40 mL) and anhydrous ethanol (30 mL) at room temperature under nitrogen, and the mixture was stirred for 1.5 h, at which point TLC analysis of the mixture (7:3 hexanes/ethyl acetate) indicated completion of the reaction. The mixture was diluted with saturated aqueous sodium bicarbonate solution (100 mL), poured into water (300 mL) and extracted with ethyl acetate (3×100 mL). The combined organic extract solvents were removed under reduced pressure and the residue was purified by column chromatography on silica gel, eluting with heptane/ethyl acetate (2:1), to provide compound A3 as a white solid (7.0 g, 66%).

Step 3. Preparation of compound A4. A mixture of compound A3 (7.0 g, 20.3) and palladium on carbon (3.0 g, 10 wt. %) in anhydrous ethyl acetate (200 mL) was shaken under an atmosphere of hydrogen (1 atmosphere) at room temperature for 1 h, at which point TLC analysis of the mixture (2:1 hexanes/ethyl acetate) indicated completion of the reaction. The atmosphere was exchanged for nitrogen and the mixture was filtered through a pad of Celite under reduced pressure, washing the filter cake with ethyl acetate (50 mL). The filtrate solvents were treated with 10% aqueous hydrochloric acid solution (100 mL) and the biphasic mixture was stirred for 30 min. The mixture was extracted with ethyl acetate (2×100 mL) and the combined organic extracts were washed sequentially with saturated aqueous sodium bicarbonate and saturated aqueous sodium chloride solutions (50 mL each), dried with anhydrous sodium sulfate and filtered. The solvents were removed under reduced pressure and the residue was purified by column chromatography on silica gel, eluting with heptane/ethyl acetate (4:1), to provide compound A4 as a colorless oil (3.9 g, 60%).

Step 4. Preparation of compound A5. Sodium hydride (1.7 g, 45 mmol, 60% in mineral oil) was added portionwise to a solution of trimethylsulfoxonium iodide (9.1 g, 45 mmol) in anhydrous dimethyl sulfoxide (100 mL) at room temperature under nitrogen, and the mixture was stirred for 1 h, after which a solution of compound A4 (9.5 g, 29.8 mmol) in anhydrous dimethyl sulfoxide (100 mL) was added. The resulting mixture was stirred at room temperature for 12 h, at which point TLC analysis of the mixture (7:3 hexanes/ethyl acetate) indicated completion of the reaction. The mixture was diluted with water (500 mL) and extracted with methyl tert-butyl ether (2×300 mL). The combined organic extracts were washed with water (2×300 mL), dried with anhydrous magnesium sulfate and filtered. The solvents were removed under reduced pressure to provide compound A5 as a colorless oil that was used in the next step without further purification (7.5 g, 76%).

Step 5. Preparation of compound A6. Lithium aluminum hydride (67 mL, 67 mmol, 1 M solution in tetrahydrofuran) was added to a solution of crude compound A5 (7.5 g, 22.2 mmol) in anhydrous tetrahydrofuran (5 mL) at 0° C. under nitrogen, after which the mixture was slowly warmed to room temperature, stirring for a total of 2 h, at which point TLC analysis of the mixture (7:3 hexanes/ethyl acetate) indicated completion of the reaction. The mixture was carefully treated with water (10 mL) followed by saturated aqueous sodium chloride solution (30 mL) and extracted with ethyl acetate (3×50 mL). The combined organic extracts were dried with anhydrous magnesium sulfate, filtered and the solvents were removed under reduced pressure to provide compound A6 as a colorless oil that was used in the next step without further purification (5.5 g, 74%): LCMS m/z 319 [M+H–H$_2$O]$^+$.

Step 6. Preparation of compound A7. Pyridinium chlorochromate (4.0 g, 19 mmol) was added in one portion to a solution of crude compound A6 (4.2 g, 12.5 mmol) in anhydrous dichloromethane (100 mL) at 0° C. under nitrogen. The mixture was slowly warmed to room temperature, stirring for a total of 3 h, at which point TLC analysis of the mixture (7:3 hexanes/ethyl acetate) indicated completion of the reaction. The solids were removed by filtration and the filtrate solvents were removed under reduced pressure. The residue was purified by column chromatography on silica gel, eluting with heptane/ethyl acetate (7:3), to provide compound A7 as a light yellow solid (2.1 g, 50%): LCMS m/z 317 [M+H–H$_2$O]$^+$.

Step 7. Preparation of compound A8. Potassium tert-butoxide (4.3 g, 38 mmol) was added to a mixture of ethyltriphenylphosphonium bromide (14.2 g, 38 mmol) in anhydrous tetrahydrofuran (30 mL) at room temperature under nitrogen, after which the mixture was heated to 80° C. and stirred for 1 h. A solution of compound A7 (3.1 g, 9.3 mmol) in anhydrous tetrahydrofuran (10 mL) was added, after which stirring at 80° C. was continued for 2 h, at which point TLC analysis of the mixture (7:3 hexanes/ethyl acetate) indicated completion of the reaction. The cooled mixture was diluted with water (30 mL) and saturated aqueous sodium chloride solution (20 mL) and extracted with ethyl acetate (2×100 mL). The combined organic extract solvents were removed under reduced pressure and the residue was purified by column chromatography on silica gel, eluting with heptane/ethyl acetate (7:3), to provide compound A8 as an off-white solid (2.0 g, 66%): LCMS m/z 329 [M+H−H$_2$O]$^+$.

Step 8. Preparation of compound A9. Borane-tetrahydrofuran complex (20.0 mL, 20 mmol, 1 M solution in tetrahydrofuran) was added to a solution of compound A8 (2.0 g, 5.8 mmol) in anhydrous tetrahydrofuran (15 mL) at 0° C. under nitrogen, after which the mixture was slowly warmed to room temperature, stirring for a total of 1 h. The mixture was cooled in an ice bath and 10% aqueous sodium hydroxide solution (12 mL) was slowly added, followed by 30% aqueous hydrogen peroxide solution (12 mL). The resulting mixture was warmed to room temperature and stirred for 1 h, at which point TLC analysis of the mixture (7:3 hexanes/ethyl acetate) indicated completion of the reaction. The mixture was extracted with dichloromethane (2×100 mL) and the combined organic extracts were washed with saturated aqueous sodium chloride solution (25 mL), dried with sodium sulfate and filtered. The solvents were removed under reduced pressure to provide crude compound A9 as a white solid that was used in the next step without further purification (2.5 g, >99%).

Step 9. Preparation of compound 1. Pyridinium chlorochromate (2.4 g, 11 mmol) was added in one portion to a solution of crude compound A9 (2.5 g, 6.9 mmol) in anhydrous dichloromethane (30 mL) at 0° C. under nitrogen. The mixture was slowly warmed to room temperature, stirring for a total of 2 h, at which point TLC analysis of the mixture (7:3 hexanes/ethyl acetate) indicated completion of the reaction. The solids were removed by filtration and the filtrate solvents were removed under reduced pressure. The residue was purified by column chromatography on silica gel, eluting with heptane/ethyl acetate (7:3), to provide 1 as an off-white solid (1.5 g, 61%). $^1$H NMR: (500 MHz, CDCl$_3$), δ (ppm), 3.49 (AB, 1H), 3.39 (AB, 1H), 3.31 (s, 3H), 2.56 (t, 1H), 2.14 (s, 3H), 1.25 (s, 3H), 0.65 (s, 3H).

Example 2. Preparation of Compound 2

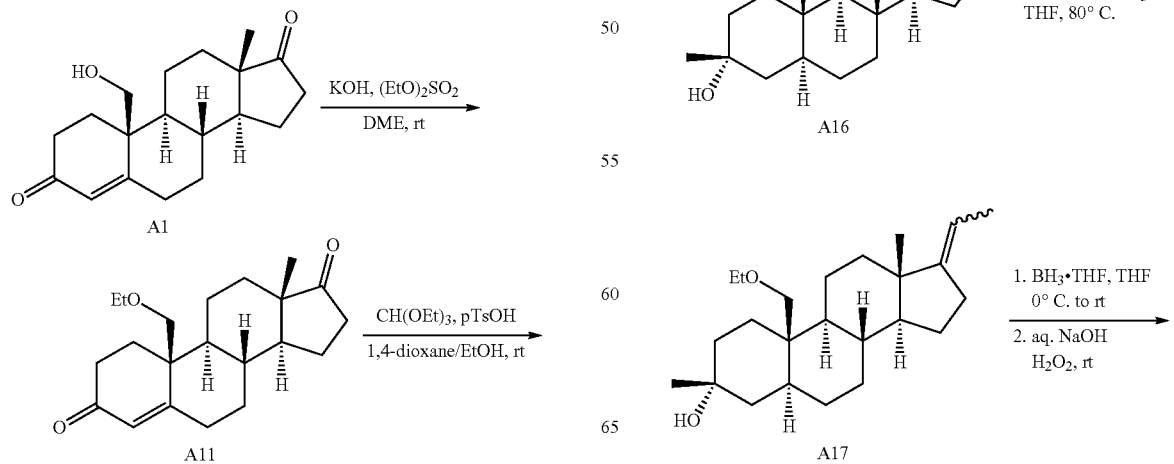

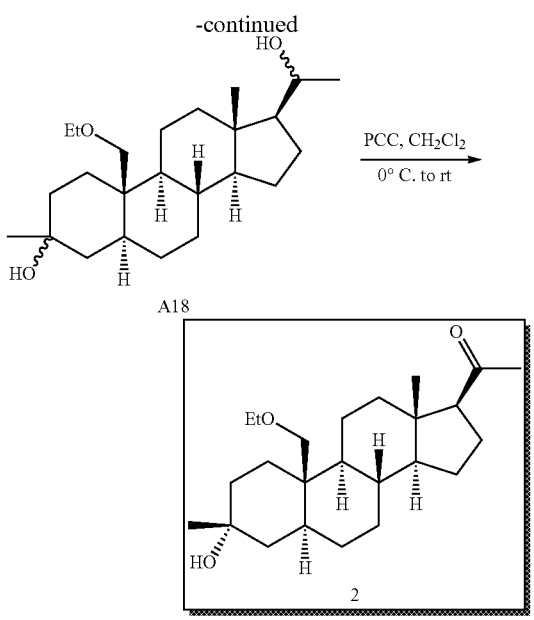

A18

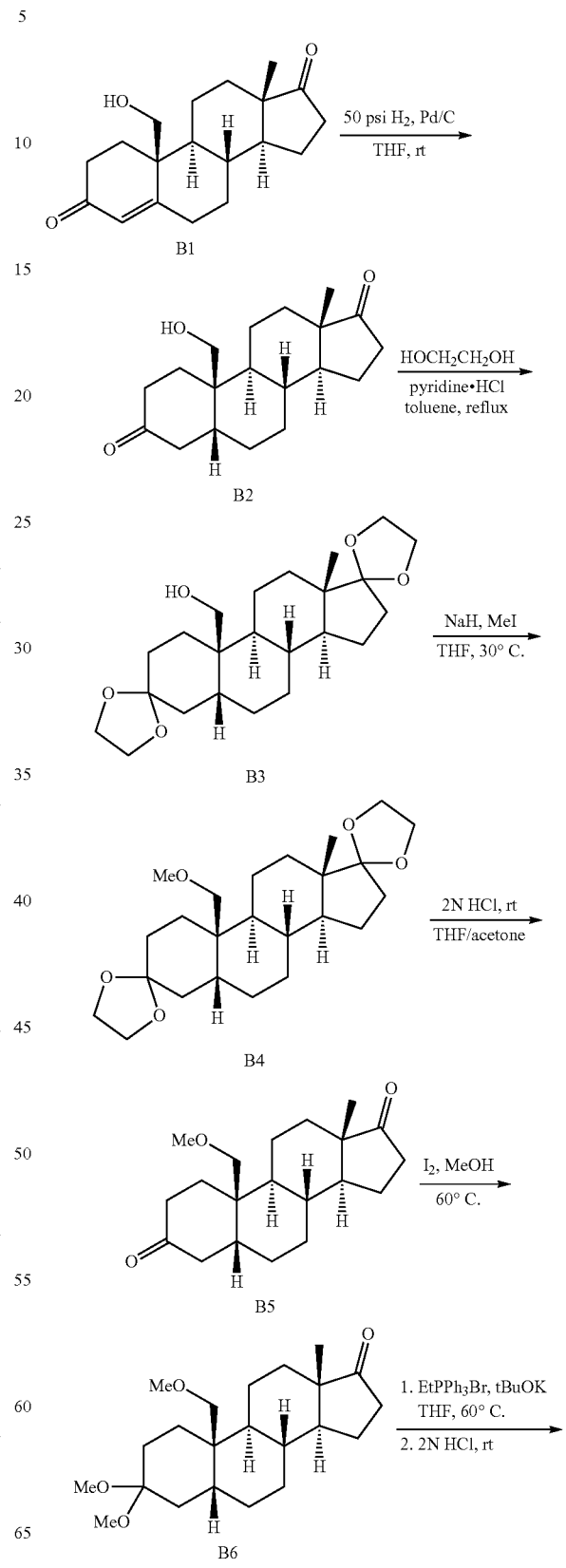

Step 1. Preparation of compound A11. Prepared according General Procedure A, Step 1 from 1 (10.0 g, 33 mmol) and ethyl sulfate (17.3 mL, 132 mmol), with purification by column chromatography on silica gel to provide compound A11 as a yellow oil (4.6 g, 42%).

Step 2. Preparation of compound A12. Prepared according General Procedure A, Step 2 from compound A11 (4.6 g, 14 mmol) to provide crude compound A12 as a yellow oil that was used in the next step without further purification.

Step 3. Preparation of compound A13. Prepared according General Procedure A, Step 3 from crude compound A1, with purification by column chromatography on silica gel to provide compound A13 as a yellow oil (1.5 g, 31%).

Step 4. Preparation of compound A14. Prepared according General Procedure A, Step 4 from compound A13 (1.7 g, 5.1 mmol) to provide crude compound A14 as a yellow oil that was used in the next step without further purification.

Step 5. Preparation of compound A15. Prepared according General Procedure A, Step 5 from crude compound A14 to provide crude compound A15 as a yellow oil that was used in the next step without further purification.

Step 6. Preparation of compound A16. Prepared according General Procedure A, Step 6 from crude compound A15, with purification by column chromatography on silica gel to provide compound A16 as an off-white solid (751 mg, 40%).

Step 7. Preparation of compound A17. Prepared according General Procedure A, Step 7 from compound A16 (750 mg, 2.2 mmol), with purification by column chromatography on silica gel to provide compound A17 as a colorless oil (757 mg, 97%).

Step 8. Preparation of compound A18. Prepared according General Procedure A, Step 8 from compound A17 (757 mg, 2.1 mmol), to provide crude compound A18 as a yellow oil that was used in the next step without further purification.

Step 9. Preparation of 2. Prepared according General Procedure A, Step 9 from crude compound A18, with purification by column chromatography on silica gel to provide 2 as a white solid (515 mg, 65%): mp 106-107° C.; $^1$HNMR (500 MHz, CDCl$_3$) δ 3.51 (d, 1H), 3.43-3.36 (m, 3H), 2.53 (t, 1H), 2.18-1.96 (m, 6H), 1.74-0.92 (m, 25H), 0.84-0.82 (m, 1H), 0.62 (s, 3H) ppm; ESI MS m/z 359 [M+H–H$_2$O]$^+$.

Example 3. General Procedure C: Preparation of Compound 3

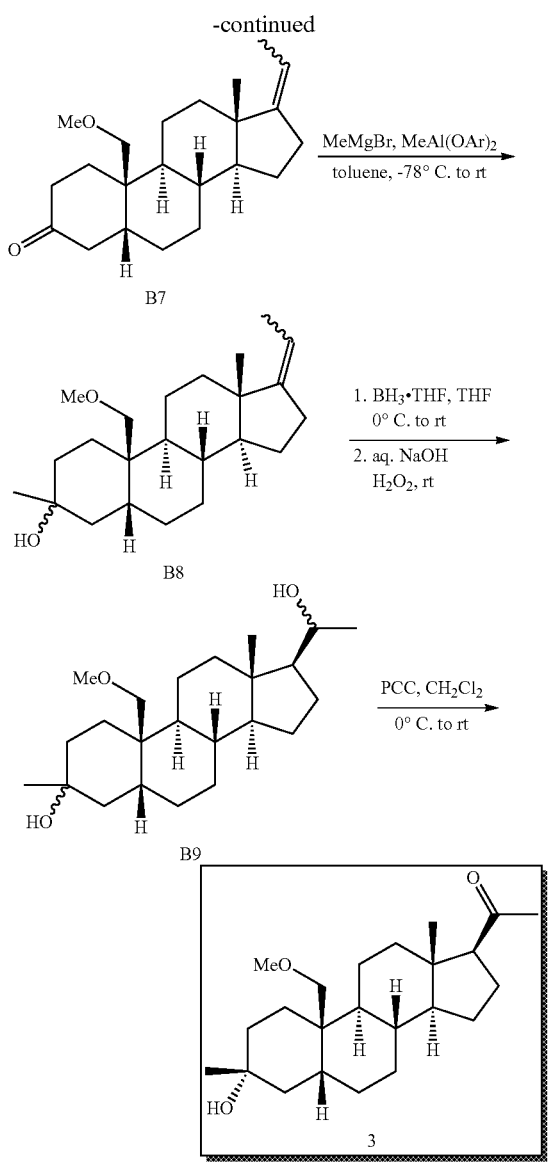

Step 1. Preparation of compound B2. A mixture of commercially available 19-hydroxyandrost-4-ene-3,17-dione (A1, 13.6 g, 45 mmol) and palladium on carbon (3.2 g, 10 wt. %) in anhydrous tetrahydrofuran (150 mL) was shaken under an atmosphere of hydrogen (50 psi) at room temperature for 12 h, at which point TLC analysis of the mixture (2:1 hexanes/ethyl acetate) indicated completion of the reaction. The atmosphere was exchanged for nitrogen and the mixture was filtered through a pad of Celite under reduced pressure, washing the filter cake with ethanol. The filtrate solvents were removed under reduced pressure to provide B2 as a white solid that was used in the next step without further purification (13.0 g, 95%): LCMS m/z 305 [M+H]$^+$.

Step 2. Preparation of compound B3. Pyridine hydrochloride (750 mg, 6.5 mmol) was added to a solution of crude compound B2 (15.0 g, 49 mmol) in ethylene glycol (65 mL) and anhydrous toluene (180 mL) at room temperature under nitrogen. The mixture was heated at reflux for 12 h with water removal by Dean-Stark apparatus, at which point TLC analysis of the mixture (2:1 hexanes/ethyl acetate) indicated completion of the reaction. The solvents were removed from the cooled mixture under reduced pressure and the residue was treated with saturated aqueous sodium chloride solution (50 mL) and extracted with ethyl acetate (3×50 mL). The combined organic extracts were washed with saturated aqueous sodium chloride solution (3×10 mL), dried with anhydrous sodium sulfate and filtered. The solvents were removed under reduced pressure to provide compound B3 as a colorless oil that was used in the next step without further purification (20.3 g, >99%): $^1$H NMR (300 MHz, CDCl$_3$) δ 4.11-3.81 (m, 8H), 3.60-3.54 (m, 1H), 2.05-1.92 (m, 3H), 1.81-163 (m, 4H), 1.59-1.35 (m, 12H), 1.28-1.12 (m, 5H), 0.8 (s, 3H) ppm; LCMS m/z 393 [M+H]$^+$.

Step 3. Preparation of compound B4. A solution of crude compound B3 (20.3 g, 49 mmol) in anhydrous tetrahydrofuran (120 mL) was added dropwise to a suspension of sodium hydride (7.9 g, 197 mmol, 60% in mineral oil) in anhydrous tetrahydrofuran (120 mL) at 0° C. under nitrogen, after which the mixture was stirred at 0° C. for 30 min. Iodomethane (15.3 mL, 246 mmol) was added dropwise, after which the mixture was heated to 35° C. and stirred for 3 h, at which point TLC analysis of the mixture (3:1 hexanes/ethyl acetate) indicated completion of the reaction. The cooled mixture was treated with saturated ammonium chloride solution (100 mL) and extracted with ethyl acetate (2×50 mL). The combined organic extracts were washed with saturated aqueous sodium chloride solution (2×20 mL), dried with anhydrous sodium sulfate and filtered. The solvents were removed under reduced pressure to provide crude compound B4 as a yellow oil that was used in the next step without further purification (25.6 g, >99%): LCMS m/z 407 [M+H]$^+$.

Step 4. Preparation of compound B5. A mixture of crude compound B4 (25.5 g, 49 mmol) in tetrahydrofuran (150 mL) and acetone (90 mL) at room temperature was treated with 2N HCl (123 mL) and the mixture was stirred for 16 h, at which point TLC analysis of the mixture (2:1 hexanes/ethyl acetate) indicated completion of the reaction. The reaction mixture was adjusted to pH 8 with slow addition of saturated aqueous sodium bicarbonate solution and extracted with ethyl acetate (3×125 mL). The combined organic extracts were washed with saturated aqueous sodium chloride solution (2×20 mL), dried with anhydrous sodium sulfate and filtered. The solvents were removed under reduced pressure and the residue was purified by column chromatography on silica gel, eluting with hexanes/ethyl acetate (2:1), to provide compound B5 as a white solid (10.6 g, 67%): $^1$H NMR (300 MHz, CDCl$_3$) δ 3.62-3.59 (m, 1H), 3.36-3.33 (m, 4H), 2.67-2.63 (m, 1H), 2.58-2.45 (m, 1H), 2.42-2.27 (m, 3H), 2.25-1.84 (m, 6H), 1.71-1.23 (m, 11H), 0.89 (s, 3H) ppm; LCMS m/z 319 [M+H]$^+$.

Step 5. Preparation of compound B6. Iodine (84 mg, 0.3 mmol) was added to a solution of compound B5 (10.6 g, 33 mmol) in anhydrous methanol (200 mL) at room temperature under nitrogen, after which the mixture was heated to 60° C. and stirred for 90 min, at which point TLC analysis of the mixture (2:1 hexanes/ethyl acetate) indicated completion of the reaction. The cooled mixture was treated with 1N sodium hydroxide solution (200 mL) and extracted with hexanes/ethyl acetate (3:1, 3×100 mL). The combined organic extracts were washed with saturated aqueous sodium chloride solution (2×25 mL), dried with anhydrous sodium sulfate and filtered. The solvents were removed under reduced pressure to provide compound B6 as a colorless oil that was used in the next step without further purification (13.8 g, >99%); LCMS m/z 365 [M+H]$^+$.

Step 6. Preparation of compound B7. Potassium tert-butoxide (11.2 g, 100 mmol) was added to a mixture of ethyltriphenylphosphonium bromide (36.9 g, 100 mmol) in anhydrous tetrahydrofuran (150 mL) at room temperature under nitrogen, after which the mixture was heated to 60° C. and stirred for 4 h. A solution of compound B6 (13.8 g, 33 mmol) in anhydrous tetrahydrofuran (100 mL) was added, after which stirring at 60° C. was continued for 18 h. The cooled mixture was diluted with water (200 mL) and hexanes (100 mL) and extracted with ethyl acetate (3×100 mL). The combined organic extracts were washed with saturated aqueous sodium chloride solution (2×25 mL), treated with 2N HCl (100 mL) and stirred at room temperature for 3 h. The resulting mixture was washed with saturated aqueous sodium bicarbonate and saturated aqueous sodium chloride solutions, dried with sodium sulfate and filtered. The solvents were removed under reduced pressure and the residue was purified by column chromatography on silica gel, eluting with hexanes/ethyl acetate (9:1), to provide compound B7 as a colorless oil (9.2 g, 84%): LCMS m/z 331 [M+H]+.

Step 7. Preparation of compound B8. Bis(2,6-di-tert-butyl-4-methylphenoxide)methylaluminum (40.6 mL, 16 mmol, 0.4 M in toluene) was added in one portion to a solution of compound B7 (1.8 g, 5.4 mmol) in anhydrous toluene (20 mL) at −78° C. under nitrogen, after which the mixture was stirred for 10 min. Methylmagnesium bromide (11.6 mL, 16 mmol, 1.4 M in tetrahydrofuran/toluene) was added dropwise, after which the mixture was stirred at −78° C. for 1 h. The mixture was warmed to ice bath temperature and slowly treated with 2N HCl (60 mL), warmed to room temperature and extracted with ethyl acetate (3×50 mL). The combined organic extracts were washed with saturated aqueous sodium chloride solution (2×20 mL), dried with sodium sulfate and filtered. The solvents were removed under reduced pressure and the residue was purified by column chromatography on silica gel, eluting with hexanes/ethyl acetate (2:1), to provide crude compound B8 as a white semi-solid (1.5 g, 91%); LCMS m/z 347 [M+H]+.

Step 8. Preparation of compound B9. Borane-tetrahydrofuran complex (27.6 mL, 27.6 mmol, 1.0 M solution in tetrahydrofuran) was added to a solution of compound B8 (2.4 g, 6.9 mmol) in anhydrous tetrahydrofuran (24 mL) at 0° C. under nitrogen, after which the mixture was slowly warmed to room temperature, stirring for a total of 4 h. The mixture was cooled in an ice bath and 10% aqueous sodium hydroxide solution (20 mL) was slowly added, followed by 30% aqueous hydrogen peroxide solution (20 mL). The resulting mixture was warmed to room temperature and stirred for 1 h and then treated with saturated aqueous sodium chloride solution (100 mL) and extracted with dichloromethane (3×100 mL). The combined organic extracts were washed with saturated aqueous sodium chloride solution (25 mL), dried with sodium sulfate and filtered. The solvents were removed under reduced pressure to provide crude compound B9 as a white solid that was used in the next step without further purification (2.7 g, >99%); LCMS m/z 365 [M+H]+.

Step 9. Preparation of 3. Pyridinium chlorochromate (6.0 g, 28 mmol) was added in one portion to a solution of compound B9 (2.7 g, 6.9 mmol) in dichloromethane (100 mL) at 0° C. under nitrogen, after which the mixture was slowly warmed to room temperature, stirring for a total of 16 h. The solids were removed by filtration and the filtrate solvents were removed under reduced pressure. The residue was semi-purified by column chromatography on silica gel, eluting with hexanes/ethyl acetate (1:1), followed by further purification by reverse phase preparative HPLC to provide 3 as a white solid (2.15 g, 86%): mp 142-144° C.; 1HNMR (300 MHz, CDCl3) δ 3.55 (d, 1H), 3.33 (s, 3H), 3.19 (d, 1H), 2.53 (t, 1H), 2.21-2.11 (m, 4H), 2.08-1.87 (m, 3H), 2.14-1.91 (m, 7H), 1.77-1.36 (m, 16H), 1.28 (s, 3H), 1.26-1.07 (m, 2H), 0.60 (s, 3H) ppm; LCMS m/z 345 [M+H−H2O]+.

Example 4. General Procedure D: Preparation of 4

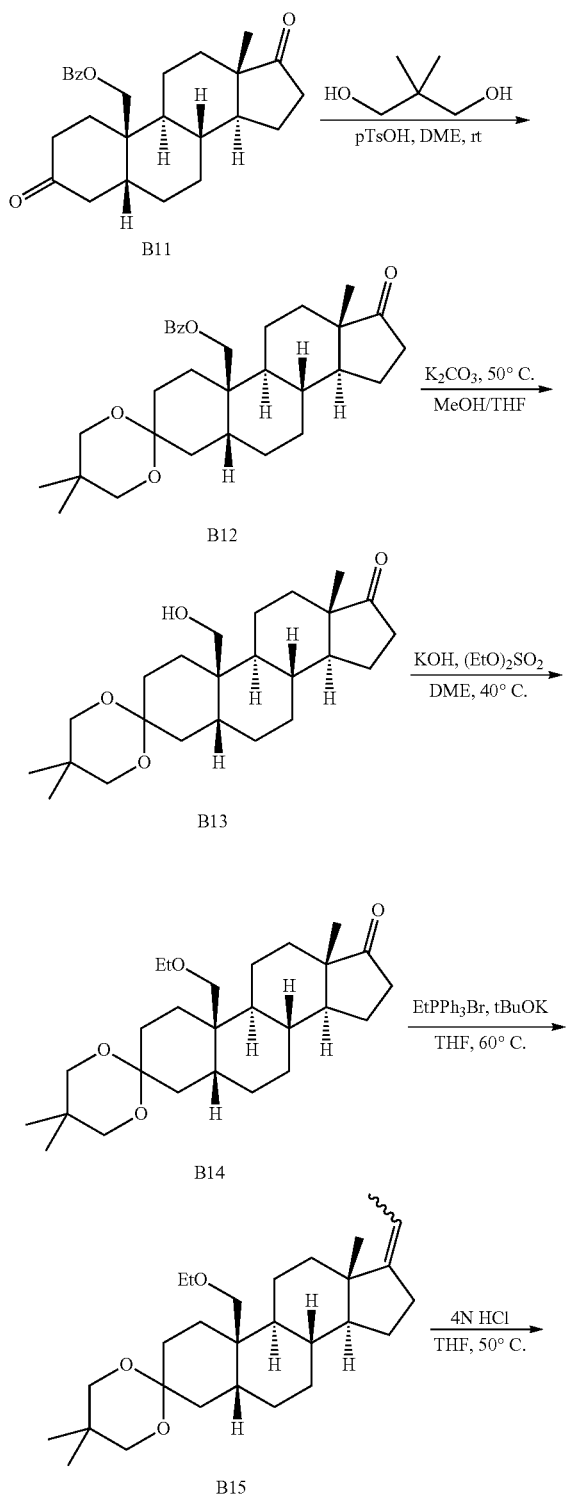

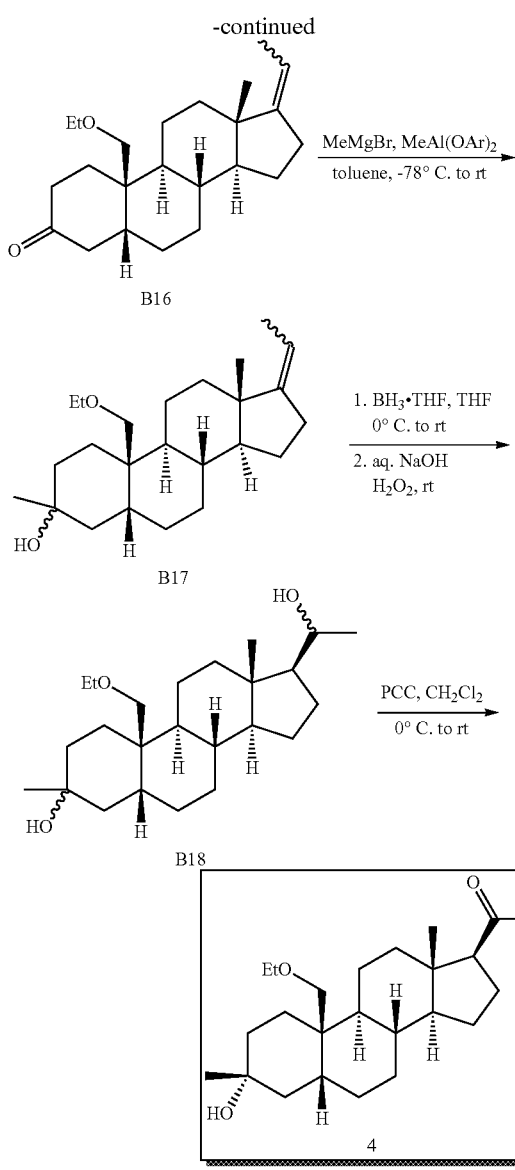

Step 1. Preparation of compound B12. 2,2-Dimethylpropane-1,3-diol (6.1 g, 59 mmol) and p-toluenesulfonic acid (931 mg, 4.9 mmol) were added to a solution of B11 (20.0 g, 49.0 mmol) in anhydrous 1,2-dimethoxyethane (300 mL) at room temperature under nitrogen, and the mixture was stirred for 12 h, at which point TLC analysis of the mixture (7:3 hexanes/ethyl acetate) indicated completion of the reaction. The solvents were removed under reduced pressure and the residue was purified by column chromatography on silica gel, eluting with heptane/ethyl acetate (1:1), to provide compound B12 as an off-white solid (10.5 g, 43%): LCMS m/z 495 [M+H]$^+$.

Step 2. Preparation of compound B13. Potassium carbonate (16.4 g, 119 mmol) was added to a solution of compound B12 (9.8 g, 19.8 mmol) in anhydrous methanol (150 mL) and anhydrous tetrahydrofuran (70 mL) at room temperature under nitrogen, after which the mixture was heated to 50° C. to stir for 12 h, at which point TLC analysis of the mixture (7:3 hexanes/ethyl acetate) indicated completion of the reaction. The solvents were removed under reduced pressure and the residue was treated with water (100 mL) and extracted with ethyl acetate (3×100 mL). The combined organic extracts were washed with saturated aqueous sodium chloride solution (40 mL), dried with sodium sulfate and filtered. The solvents were removed under reduced pressure and the residue was purified by column chromatography on silica gel, eluting with hexanes/ethyl acetate (1:4), to provide compound B13 as an off-white solid (5.8 g, 75%): LCMS m/z 391 [M+H]$^+$.

Step 3. Preparation of compound B14. Finely-ground potassium hydroxide (4.7 g, 85 mmol) was added to a solution of compound B13 (5.5 g, 14.1 mmol) in anhydrous 1,2-dimethoxyethane (200 mL) at 0° C. under nitrogen, after which ethyl sulfate (8.7 g, 56 mmol) was added portionwise. The mixture was slowly warmed to room temperature and then heated to 40° C., stirring for a total of 12 h, at which point TLC analysis of the mixture (7:3 hexanes/ethyl acetate) indicated completion of the reaction. The mixture was diluted with water (200 mL) and extracted with ethyl acetate (3×200 mL). The combined organic extracts were washed with saturated aqueous sodium chloride solution (100 mL), dried with anhydrous sodium sulfate and filtered. The solvents were removed under reduced pressure and the residue was semi-purified by column chromatography on silica gel, eluting with heptane/ethyl acetate (4:1), to provide semi-pure compound B14 as a yellow oil that was used in the next step without further purification: LCMS m/z 419 [M+H]$^+$.

Step 4. Preparation of compound B15. Potassium tert-butoxide (5.02 g, 44 mmol) was added to a mixture of ethyltriphenylphosphonium bromide (16.5 g, 44 mmol) in anhydrous tetrahydrofuran (150 mL) at room temperature under nitrogen, after which the mixture was heated to 60° C. and stirred for 12 h. A solution of compound B14 (6.2 g, 14.8 mmol) in anhydrous tetrahydrofuran (50 mL) was added, after which stirring at 60° C. was continued for 18 h. The cooled mixture was diluted with water (200 mL) and saturated aqueous sodium chloride solution (50 mL) and extracted with ethyl acetate (3×100 mL). The combined organic extracts were washed with saturated aqueous sodium chloride solution (50 mL), dried with sodium sulfate and filtered. The solvents were removed under reduced pressure and the residue was purified by column chromatography on silica gel, eluting with hexanes/ethyl acetate (9:1), to provide compound B15 as a light yellow oil (3.6 g, 57%): LCMS m/z 431 [M+H]$^+$.

Step 5. Preparation of compound B16. A mixture of crude compound B15 (3.5 g, 8.1 mmol) in tetrahydrofuran (10 mL) at room temperature was treated with 4N HCl (10 mL), after which the mixture was heated to 50° C. and stirred for 4 h, at which point TLC analysis of the mixture (2:1 hexanes/ethyl acetate) indicated completion of the reaction. The solvents were removed under reduced pressure and the residue was semi-purified by column chromatography on silica gel, eluting with heptane/ethyl acetate (1:19), to provide semi-pure compound B16 as a yellow oil: LCMS m/z 345 [M+H]$^+$.

Step 6. Preparation of compound B17. Prepared according General Procedure C, Step 7 from semi-pure compound B16 (500 mg, 1.4 mmol) to provide semi-pure compound B17 as a yellow oil that was used in the next step without further purification: LCMS m/z 361 [M+H]$^+$.

Step 7. Preparation of compound B18. Prepared according General Procedure C, Step 8 from semi-pure compound B17 to provide semi-pure compound B18 as a colorless oil that was used in the next step without further purification: LCMS m/z 379 [M+H]$^+$.

Step 9. Preparation of 4. Prepared according General Procedure C, Step 9 from semi-pure compound B18, with semi-purification by column chromatography on silica gel followed by further purification by reverse phase preparative HPLC to provide 4 as an off-white solid (110 mg, 22%): mp 46-48° C.; ¹HNMR (300 MHz, CDCl₃) δ 3.57 (d, 1H), 3.44 (q, 2H), 3.21 (d, 1H), 2.53 (t, 1H), 2.14-1.87 (m, 8H), 1.83-1.41 (m, 13H), 1.28-1.12 (m, 11H), 0.59 (s, 3H) ppm; LCMS m/z 359 [M+H–H₂O]⁺.

Example 5. Preparation of 5

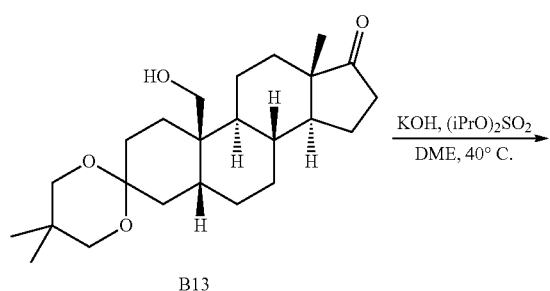

B13

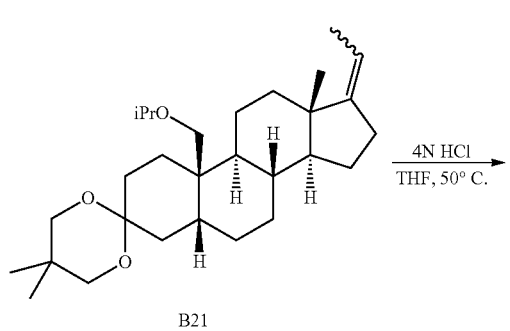

B20

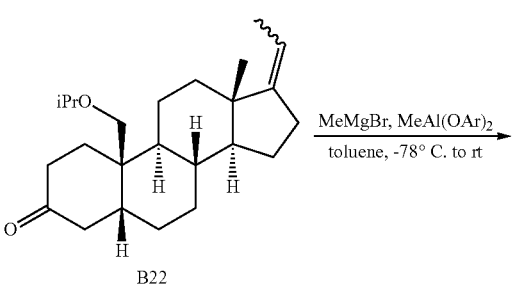

B21

B22

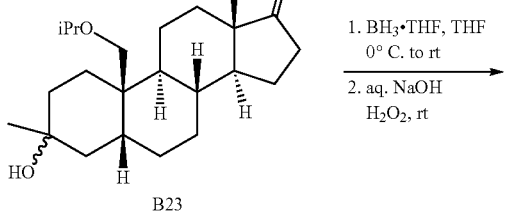

B23

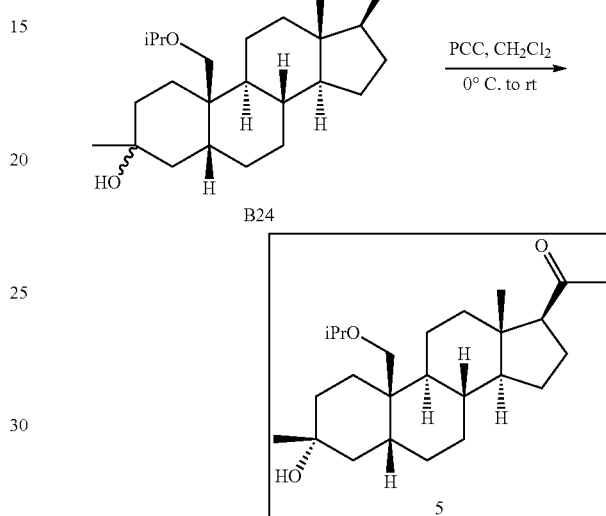

B24

5

Step 1. Preparation of compound B20. Prepared according General Procedure C, Step 3 from compound B13 (4.5 g, 11.4 mmol) and isopropyl sulfate (11.4 mL, 68.7 mmol), with purification by column chromatography on silica gel to provide compound B20 as a light yellow oil (1.6 g, 32%): LCMS m/z 433 [M+H]⁺.

Step 2. Preparation of compound B21. Prepared according General Procedure C, Step 4 from compound B20 (1.6 g, 3.7 mmol) to provide crude compound B21 as a light yellow oil: LCMS m/z 445 [M+H]⁺.

Step 3. Preparation of compound B22. Prepared according General Procedure C, Step 5 from crude compound B21, with purification by column chromatography on silica gel to provide compound B22 as a colorless oil (1.1 g, 22%): LCMS m/z 359 [M+H]⁺.

Step 4. Preparation of compound B23. Prepared according General Procedure C, Step 6 from compound B22 (1.1 g, 3.1 mmol) to provide crude compound B23 as a colorless oil: LCMS m/z 359 [M+H]⁺.

Step 5. Preparation of compound B24. Prepared according General Procedure C, Step 7 from crude compound B23 to provide crude compound B24 as a white solid: LCMS m/z 393 [M+H]⁺.

Step 6. Preparation of 5. Prepared according General Procedure C, Step 8 from crude compound B24, with semi-purification by column chromatography on silica gel followed by further purification by reverse phase preparative HPLC to provide 5 as a white solid (340 mg, 36%): mp 44-46° C.; ¹HNMR (300 MHz, CDCl₃) δ 3.53 (d, 1H), 3.47-3.33 (m, 1H), 3.22 (d, 1H), 2.53 (t, 1H), 2.21-1.88 (m, 8H), 1.83-1.31 (m, 9H), 1.29-1.09 (m, 18H), 0.60 (s, 3H) ppm; LCMS m/z 373 [M+H−H$_2$O]$^+$.

Example 6. Preparation of 6

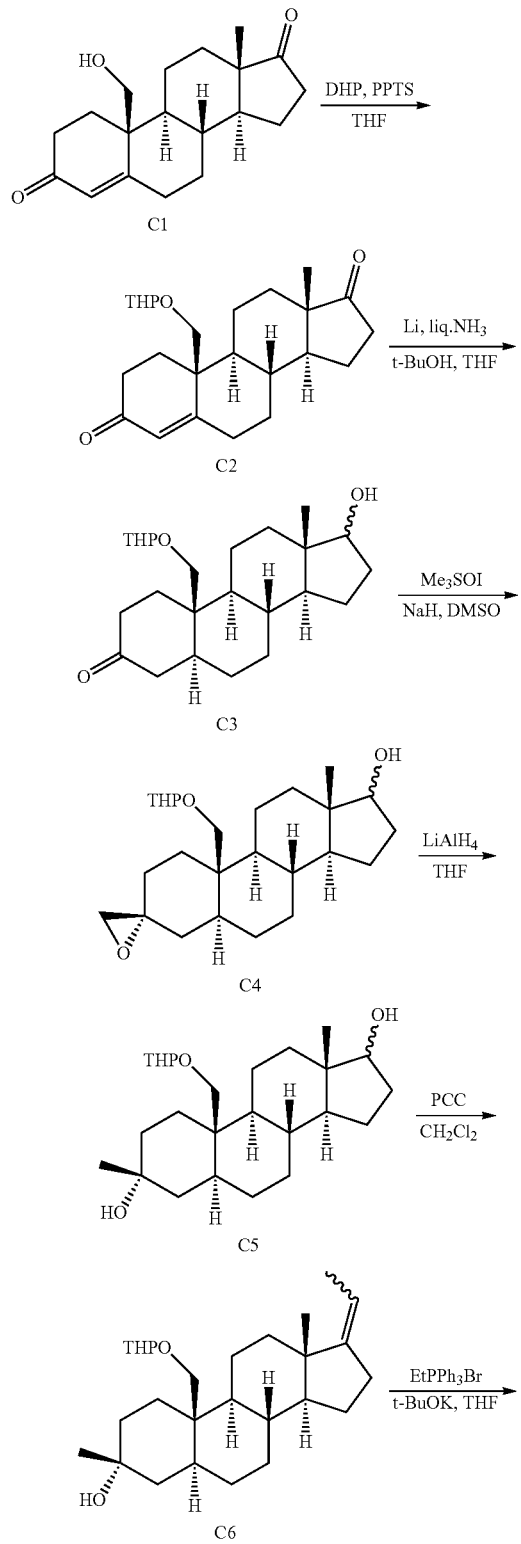

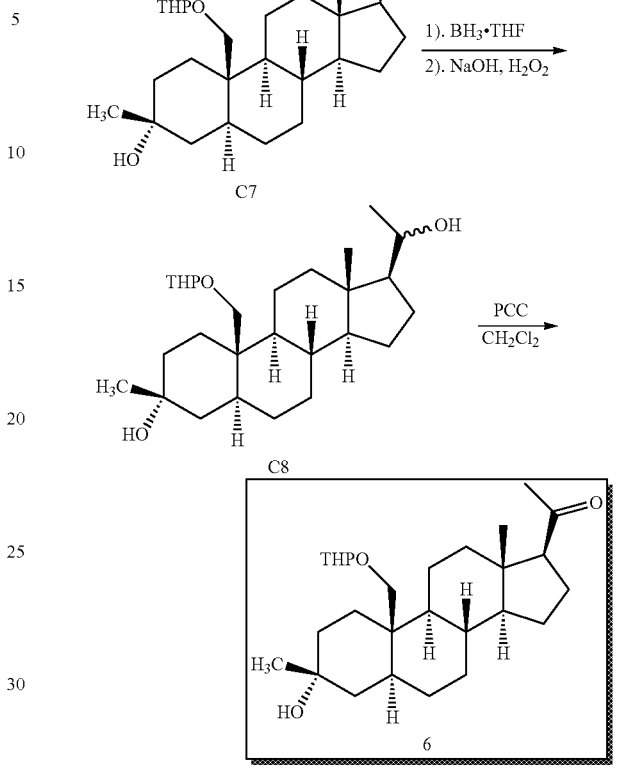

Step 1. Preparation of compound C2. Compound C1 (10.0 g, 33 mmol) was dissolved in 100 mL of THF. Dihydropyran (25 ml, 270 mmol) and PPTS (4.16, 16 mmol) was added and the resultant reaction mixture was vigorously stirred for 15 h at room temperature. Upon concentration under reduced pressure, the reaction mixture was taken up in EtOAc (500 mL), washed with water (300 mL) and brine (300 mL), dried over sodium sulfate and concentrated under reduced pressure, The residue was purified by chromatography on silica gel (eluant: petroleum ether /EtOAc=10/1~3/1) to afford compound C2 12.52 g (97.65%). LC-MS: rt=1.65 min, m/z=409.0 [M+Na]+

Step 2. Preparation of compound C3. Lithium metal (3.0 g, 0.4 mmol) were added to condensed ammonia (500 ml) in a three neck flask at −70° C. Then a solution of compound C2 (5.0 g, 13 mmol) and tert-BuOH (0.95 g, 13 mmol) in anhydrous tetrahydrofuran (100 mL) was added dropwise and stirred for 0.8 hours. Ammonium chloride (30.0 g) was added to quench the reaction and the ammonia was left to evaporate overnight. The residue was extracted with EtOAc (300 mL). The organic layers were washed with saturated NaCl solution (2×200 mL), dried over Na2SO4 and concentrated under reduced pressure, The residue was purified by chromatography on silica gel (eluant: petroleum ether /EtOAc=10/1~2/1) to afford 2.0 g of compound C3 (39.60%). LC-MS: rt=1.68 min, m/z=413.3 [M+Na]+

Step 3. Preparation of compound C4. Me3SOI (16.9 g, 76.80 mmol) was dissolved in 80 mL of DMSO and NaH (1.84 g, 76.80 mmol) was added. The mixture was stirred at room temperature for 1 hour, then compound C3 (6.0 g, 15.36 mmol) dissolved in 60 mL of DMSO was added. The solution was stirred at room temperature overnight. Water (10 mL) was then added to the reaction mixture. The aqueous reaction mixture was extracted with EtOAc (300 mL×3). The extracts were dried over Na2SO4, filtered, concentrated. The crude compound C4 was directly used in the next step without further purification.

Step 4. Preparation of compound C5. The crude compound C4 was slowly added into a suspension of LiAlH4 (1.75 g, 51 mmol) in 100 ml of dry THF at 0° C. The mixture was stirred at room temperature for 2 h, then 2.1 g of 15% aq NaOH was slowly added to quench the reaction. The reaction mixture extracted with EtOAc (200 mL×3). The organic layers were dried over MgSO4, filtered, and concentrated. The crude compound C5 was directly used in the next step without further purification.

Step 5. Preparation of compound C6. The crude compound C5 was dissolved in 100 ml of dry CH2Cl2, and 4.0 g of PCC was added at 0° C. Then the mixture was stirred at room temp for 6 h. The reaction mixture was then filtered, concentrated, and purified by flash chromatography on silica gel using 10/1~3/1 petroleum ether: ethyl acetate=10/1-3/1 elution to give compound C6, 3.10 g (50.89%, three-step yield).

Step 6. Preparation of compound C7. To a suspension of Ethyltriphenylphosphonium bromide (14.20 g, 38.3 mmol) in dry THF (40 mL) was added KOtBu (4.30 g, 38.3 mmol) under N2 atmosphere. The mixture was heated at reflux for 1 hour, during which time the mixture turned bright orange. Then compound C6 (3.1 g, 7.66 mmol) in dry THF (25 mL) was added to the above refluxing solution and stirred at reflux overnight. After cooling to room temperature, the solution was poured into brine (100 mL). The aqueous solution was extracted with ethyl acetate (100 mL×3). The extracts were washed with brine (30 mL×2), dried over Na2SO4, filtered, concentrated and purified by column chromatography on silica gel (petroleum ether /EtOAC from 10/1 to 4/1) to give compound C7 2.2 g (68.97%) as white solid. Furthermore, the C-3 isomer (0.30 g, 9.63%) was also obtained.

Step 7. Preparation of compound C8. To a solution of compound C7 (3 g, 7.2 mmol) in dry THF (20 mL) was added borane-tetrahydrofuran complex (29 mL of 1.0 M solution in THF) and the reaction mixture was stirred at ambient temperature for 1 hour. 10% aqueous NaOH (20 mL) was slowly added. The mixture was cooled in ice and 30% aqueous solution of H2O2 (20 mL) was slowly added. The mixture was stirred at ambient temperature for 1 hour and then extracted with CH2Cl2 (3×100 mL). The combined CH2Cl2 extracts were washed with 10% aqueous Na2S2O3 (50 mL), which was directly used in the next step without further purification.

Step 7. Preparation of compound 6. The combined CH$_2$Cl$_2$ extracts of the compound C8 of last step was used without further purification. 3.5 g of PCC was added at 0° C. Then the mixture was stirred at room temperature for 6 h, The mixture was filtered, concentrated, and purified by flash chromatography on silica gel using 12/1~7/1(petroleum ether:ethyl acetate) elution to give 1.28 g of compound 6 (41.23% two steps). LC-MS: rt=1.90 min,m/z=455.3[M+Na]+. 1HNMR (500 MHz, CDCl3) δ(ppm): 4.57&4.53(1H, t), 3.96&3.87(1H) 3.82 (1H,t), 3.56-3.53(1H), 3.44&3.27 (1H,AB), 2.53(1H,t), 2.12&2.11(3H,s), 1.22&1.21(3H,s), 0.64&0.61(1H,s).

Example 7. Preparation of 7

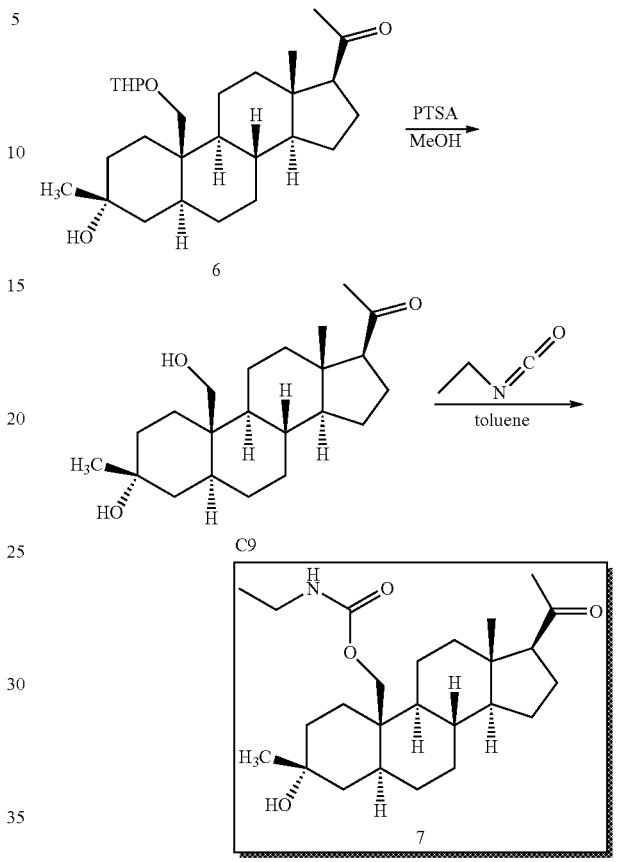

Step 1. Preparation of compound C9. Compound 6 (1.28 g, 2.96 mmol) was dissolved in 50 mL of dry MeOH and 100 mg of PTSA was added. The reaction mixture was stirred at room temperature overnight. The reaction mixture was then concentrated under reduced pressure. This product mixture was separated by flash chromatography on silica gel using 8/1~2/1 (petroleum ether:EtOAc) elution to give 674 mg of compound C9 (65.32%). LC-MS: rt=1.90 min,m/z=331.3 [M–H$_2$O+H]$^+$, m/z=349.2[M+H]$^+$. $^1$HNMR (500 MHz, CDCl3) δ(ppm): 3.89 (1H, AB), 3.72 (1H, AB), 2.53 (1H, t), 2.11 (3H, s), 1.22 (3H, s), 0.64 (3H, s). $^{13}$CNMR (125.77 MHz, CDCl3) δ(ppm): 209.78, 69.68, 63.80, 60.12, 57.07, 54.39, 44.36, 42.04, 41.18, 39.62, 39.31, 36.05, 35.39, 31.85, 31.68, 31.54, 28.04, 27.91, 24.39, 22.86, 22.75, 13.72.

Step 2. Preparation of compound 7. 30 mg of compound C9 was dissolved in toluene (3 ml) and isocyanatoethane (60 mg, 0.9 mmol) was added. The reaction mixture was heated to reflux overnight in a pressure sealed tube. After cooling to room temperature, the solvent was removed under reduced pressure and the residue was purified by silica gel (EA/PE=1:4). 10 mg of compound 7 was isolated as a white residue, (yield 25%). $^1$HNMR (400 MHz, MeOD) δ(ppm): 4.26(1H,AB), 4.03(1H,AB), 3.02 (2H,q), 2.53(1H,t), 2.01 (3H,$), 1.08 (3H, s), 0.99 (3H,t), 0.51(3H, s).

Example 8. Preparation of 8

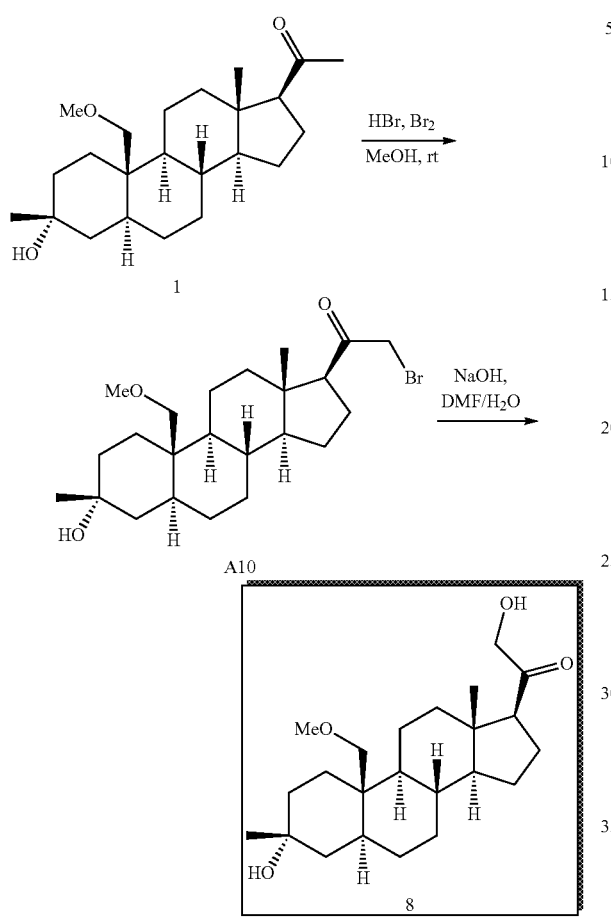

Step 1. Preparation of compound A10. Hydrogen bromide (3 drops, 48% in water) was added to a solution of 1 (1.4 g, 3.9 mmol) in anhydrous methanol (150 mL) at room temperature in the dark under nitrogen, after which bromine (0.4 mL, 7.7 mmol) was added. The mixture was stirred for 1 h, at which point TLC analysis of the mixture (7:3 hexanes/ethyl acetate) indicated completion of the reaction. The mixture was poured into ice-water (100 mL), treated with saturated aqueous sodium bicarbonate solution (30 mL) and extracted with ethyl acetate (2×60 mL). The combined organic extracts were washed with saturated aqueous sodium bicarbonate solution (4×100 mL) and saturated aqueous sodium chloride solution (50 mL), dried with magnesium sulfate and filtered. The solvents were removed under reduced pressure and the residue was purified by column chromatography on silica gel, eluting with heptane/ethyl acetate (1:1), to provide compound A10 as a colorless semi-solid (1.2 g, 71%): LCMS m/z 441 [M+H]$^+$.

Step 2. Preparation of compound 8. To a solution of compound A10 (60 mg, crude) in DMF/H$_2$O (2 mL/1 mL) was added NaOH (30 mg, 0.7 mmol). The resulting solution was stirred at room temperature for 30 min. Then TLC showed the reaction was complete. The solution was diluted with EtOAc (30 mL) and washed with brine (15 mL×2). Dried over Na$_2$SO$_4$ and concentrated, the residue was purified by column chromatography (silica gel, EtOAc/PE=3:1) to give compound 8 (10 mg, 20%) as a white solid. $^1$H NMR: (500 MHz, CDCl$_3$), δ (ppm), 4.25-4.14(m, 2H), 3.48 (AB, 1H), 3.38 (AB, 1H), 3.30 (s, 3H), 2.47 (t, 1H), 1.25 (s, 3H), 0.67 (s, 3H).

Example 9. Preparation of 9

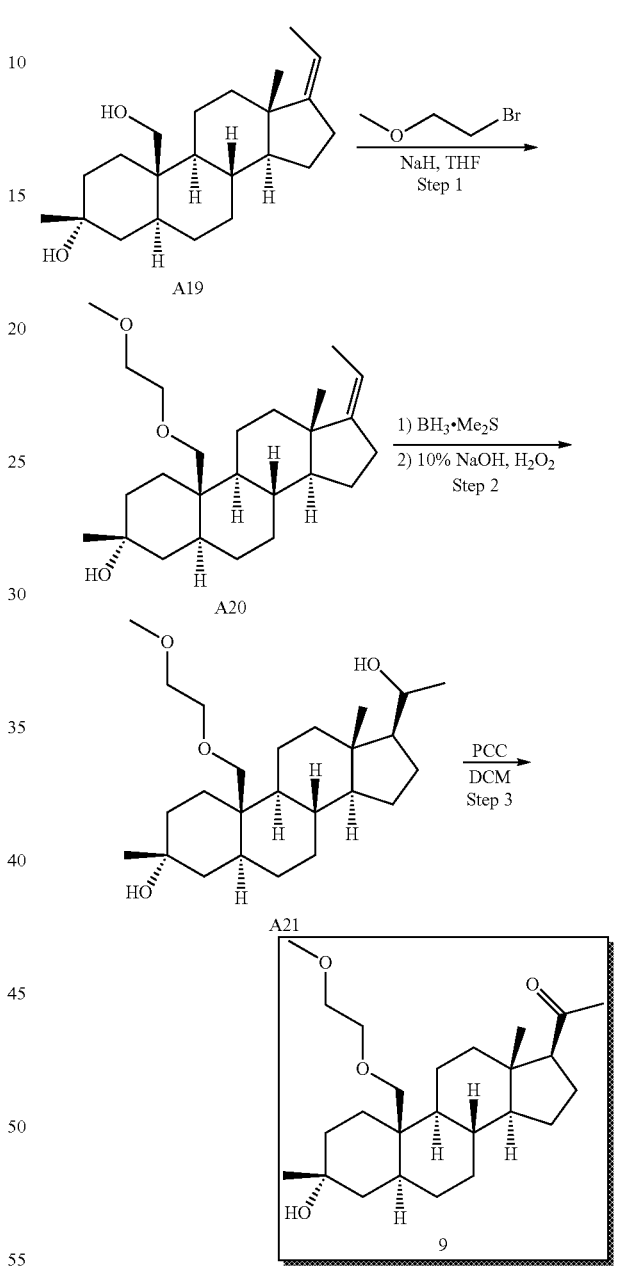

Step 1. Preparation of compound A20. To a solution of A19 (1 g, 3.00 mmol) in dry THF (10 mL) was added NaH (60%, 1.19 g, 30 mmol) in portions carefully. The suspension was stirred at 50° C. for 1 hour, and 1-bromo-2-methoxyethane (4.16 g, 30 mmol) was added to this mixture. After stirring at 50° C. for additional 16 hours, when TLC showed approximately one third of starting material was converted into product, the reaction mixture was cooled, quenched with ice water (10 mL), extracted with EtOAc (10 mL*3). The combined organic layers were dried over anhydrous sodium sulfate, filtered and concentrated. The residue was purified by column chromatography on silica gel (PE:EA=15:1). The starting material was recovered, and the procedure was repeated three times using the recovered starting material under same condition to afford A20 (total yield: 0.5 g, 42.6%) as light yellow oil. LCMS $R_f$=1.274 min in 2 min chromatography, 30-90 AB, purity 79.4%, MS ESI calcd. for $C_{25}H_{43}O_3$ [M+H]$^+$391, found 373 ([M+H−18]$^+$).

Step 2. Preparation of compound A21. To a solution of A20 (0.5 g, 1.28 mmol) in dry THF (5 mL) under nitrogen at 0° C. was added borane-dimethyl sulfide (1.28 mL, 12.8 mmol) dropwise. After stirring at 25° C. for 16 hours, when TLC (PE:EA=5:1) showed the starting material was consumed, aqueous NaOH (10%, 10 mL) was added to this mixture dropwise at 0° C. To this mixture was added hydrogen peroxide (30%, 4.33 g, 38.4 mmol). The resultant suspension was stirred at 25° C. for 1 hour. TLC (PE:EA=5:1) showed the intermediate was consumed. The reaction mixture was quenched with aqueous $Na_2S_2O_3$ (10 mL), extracted with EtOAc (10 mL*3). The combined organic layers were dried over anhydrous sodium sulfate and concentrated to give A21 (0.7 g, 77.5%, purity: 58%) as light yellow oil which was used directly without further purification. LCMS $t_R$=1.027 min in 2 min chromatography, 30-90 AB, purity 58.8%, MS ESI calcd. for $C_{25}H_{45}O_4$[M+H]$^{30}$ 409, found 431 ([M+Na]$^+$).

Step 2. Preparation of compound 9. To solution of A21 (0.7 g, 0.991 mmol, purity: 58%) in dichloromethane (15 mL) was added silica gel (1 g) and PCC (1.06 g, 4.95 mmol). After stirring at 25° C. for 16 hours, when TLC (PE:EA=5:1) showed the starting material was consumed, the mixture was filtered, and the filtrated was concentrated. The residue was purified by column chromatography on silica gel (PE:EA=15:1) to give compound 9 (0.3 g, 74.4%) as white solid. The product was divided into two batches; one batch (0.2 g) was used in next step without further purification, and another one (0.1 g) was purified by prep.HPLC to afford pure product (27 mg) for delivery. $^1$H NMR (400 MHz, CDCl$_3$) δ=3.58 (d, J=9.6 Hz, 1H), 3.51 (s, 4H), 3.45 (d, J=10.0 Hz, 1H), 3.35 (s, 3H), 2.53 (t, J=8.8 Hz, 1H), 2.20-2.15 (m, 1H), 2.11 (s, 3H), 2.07-1.97 (m, 2H), 1.72-1.60 (m, 6H), 1.54-1.47 (m, 4H), 1.37-1.25 (m, 3H), 1.21-1.06 (m, 8H), 1.01-0.91 (m, 1H), 0.86-0.79 (m, 1H), 0.62 (s, 3H). LCMS $t_R$=1.038 min in 2 min chromatography, 30-90 AB, purity 100%, MS ESI calcd. for $C_{25}H_{43}O_4$[M+H]$^+$407, found 429 ([M+Na]$^+$).

Example 10. Preparation of 10

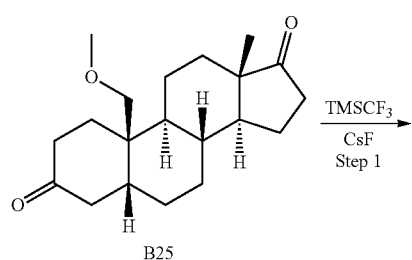

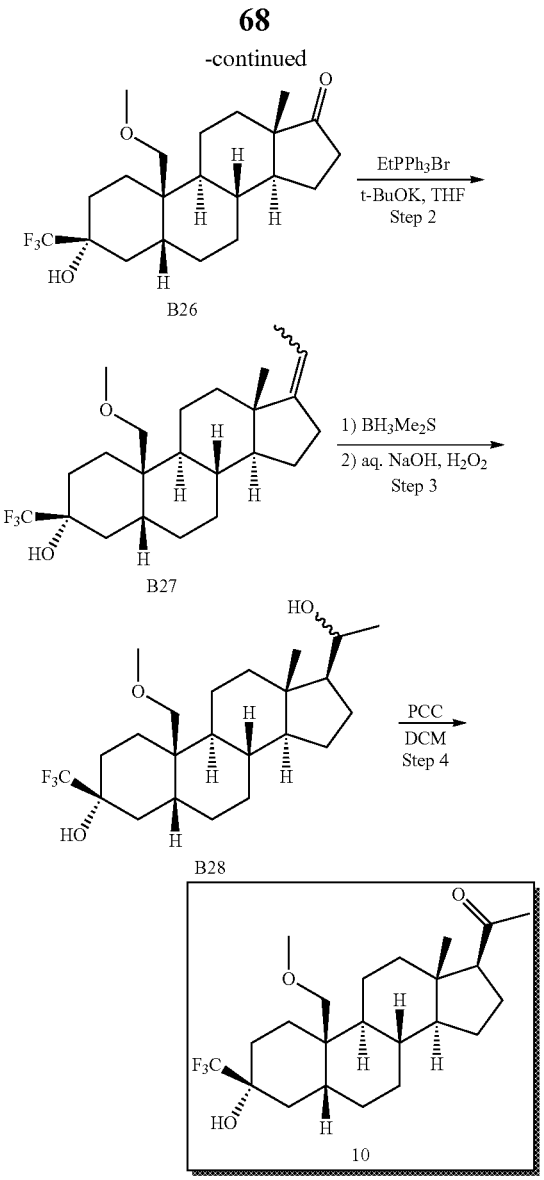

Step 1. Preparation of compound B26. To a solution of B25 (2 g, 6.28 mmol) in THF (30 mL) in a flask was added CsF (953 mg, 6.28 mmol) at 0° C., then TMSCF$_3$ (1.33 g, 9.42 mmol) was added dropwise. The reaction was allowed to warm to 25° C. and stirred for 2 h. TLC(PE:EtOAc=3:1) showed the starting material was consumed completely. Then the reaction mixture was treated with 2 M aq.HCl (10 mL) and stirred for 6 h. The reaction was then diluted with H$_2$O (30 mL) and extracted with EtOAc (30 mL×2). The combined organic layer was washed with brine (20 mL), dried over Na$_2$SO$_4$ and concentrated to get the crude product which was purified by silica gel column (PE:EtOAc=50:1 to 10:1) to afford product B26 (1.1 g, 45.0% yield) as a yellow oil. $^1$H NMR (400 MHz, CDCl$_3$) δ 3.49(d, J=8.0 Hz, 1H), 3.32-3.22(m, 4H), 2.46-2.39(m, 1H), 2.10-1.71(m, 8H), 1.68-1.10 (m, 14H), 0.85(s, 3H).

Step 2. Preparation of compound B27. To a solution of ethyltriphenylphosphonium bromide (5.19 g, 14.0 mmol) in THF (30 mL), was added t-BuOK (1.57 g, 14.0 mmol). The reaction mixture was heated to 60° C. for 1 h and B26 (1.1 g, 2.83 mmol) was added to the mixture which was stirred at 60° C. for an additional 8 h. TLC (PE:EtOAc=3:1)

showed the reaction was complete. The reaction mixture was cooled, then diluted with H$_2$O(30 mL) and extracted with EtOAc (30 mL×2). The combined organic layer was washed with brine (20 mL), dried over Na$_2$SO$_4$ and concentrated. The residue was purified by silica gel column (PE: EtOAc=100:1 to 15:1) to afford B27 (1 g, 88.6% yield) as a yellow oil. $^1$H NMR (400 MHz, CDCl$_3$) δ 5.15-5.02(m, 1H), 3.56(d, J=8.0 Hz, 1H), 2.46-2.39(m, 1H), 3.34(s, 3H), 3.29 (d, J=8.0 Hz, 1H), 2.43-1.80 (m, 7H), 1.58-1.10 (m, 19H), 0.90(s, 3H).

Step 3. Preparation of compound B28. To a solution of B27 (1 g, 2.49 mmol) in THF (15 mL) under N$_2$ protection was added dropwise a solution of BH$_3$-Me$_2$S (2.48 mL, 10 M) at 0° C. The solution was stirred at 25° C. for 4 h. TLC (PE/EtOAc=3/1) showed the reaction was complete. After cooling to 0° C., a solution of NaOH (9.93 mL, 3 M) was added very slowly, a large amount of gas released. After the addition was complete, H$_2$O$_2$ (4.53 mL, 33%) was added slowly and the inner temperature was maintained below 10° C. The resulting solution was stirred at 25° C. for 1 h. The resulting solution was extract with EtOAc (20 mL×3). The combined organic solution was washed with saturated aqueous Na$_2$S$_2$O$_3$ (20 mL×3), brine (20 mL), dried over Na$_2$SO$_4$ and concentrated in vacuum to give the crude product (1 g) as yellow oil. The crude product was used for the next step without further purification.

Step 4. Preparation of compound 10. A mixture of B28 (1.0 g, 2.38 mmol), PCC (0.767 g, 3.56 mmol) and silica gel (0.843 g, w/w=1/1.1) in DCM (15 mL) was stirred at 25° C. for 2 h, the reaction mixture color became brown. TLC (PE/EtOAc=3/1) showed the reaction was complete. The solution was filtered and the filter cake was washed with DCM (20 mL). The combined filtrate was concentrated in vacuum. The residue was purified by silica gel column eluted with PE:EtOAc=15:1 to 8:1 to give compound 10 (800 mg, 80.6%) as a white solid. MS ESI calcd. for C$_{24}$H$_{41}$O$_4$[M+H]$^+$417, found 399 ([M+H−18]$^+$). $^1$H NMR (400 MHz, CDCl$_3$) δ 3.52(d, J=8.0 Hz, 1H), 3.28(d, J=8.0 Hz, 1H), 2.58-2.52 (m, 1H), 2.20-1.60(m, 15H), 1.53-1.10(m, 11H), 0.62(s, 3H).

Example 11. Preparation of 11

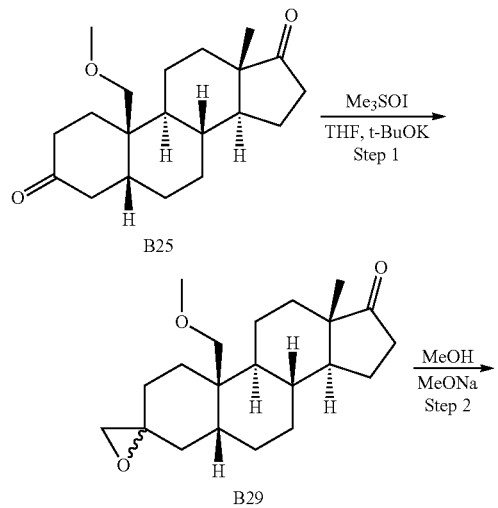

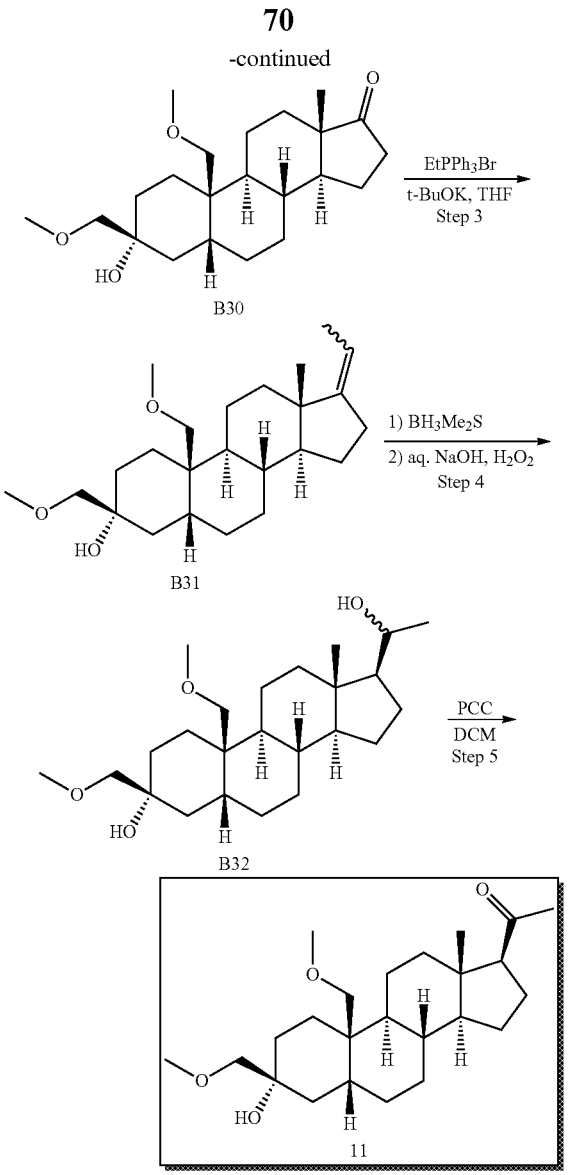

Step 1. Preparation of compound B29. To a solution of Me$_3$SOI (691 mg, 3.14 mmol) in THF (15 mL) in a flask was added t-BuOK(352 mg, 3.14 mmol). The reaction mixture was stirred at 60° C. for 1.5 h. Then a solution of B25 (200 mg, 0.63 mmol) in THF (10 mL) was added to the reaction. The reaction was stirred for 0.5 h at 30° C. After the TLC(PE:EA=3:1) showed the reaction was complete, the reaction was quenched with aq.NH$_4$Cl (30 mL). The reaction was extracted with EtOAc (20 mL×2), washed with brine (20 mL), dried over Na$_2$SO$_4$ and evaporated in vacuum to afford crude product B29 (200 mg, 96% yield) as yellow solid. $^1$H NMR (400 MHz, CDCl$_3$) δ 3.52(d, J=8.0 Hz, 1H), 3.36(d, J=8.0 Hz, 1H), 3.32(s, 3H), 2.67-2.60 (m, 2H), 2.50-2.28 (m, 2H), 2.20-2.03(m, 2H), 1.98-1.70 (m, 8H), 1.52-1.02 (m, 10H), 0.86(s, 3H).

Step 2. Preparation of compound B30. To a solution of B29 (200 mg, 0.602 mmol) in MeOH (10 mL) in a flask was added MeONa (98 mg, 1.806 mmol), the reaction mixture was then heated to 60° C. and stirred for 6 h. TLC (PE: EtOAc=3:1) showed the reaction was complete. The reaction mixture was then concentrated. The residue was purified by silica gel column (PE:EtOAc=10:1 to 5:1) to afford product B30 (150 mg, 68% yield) as white solid. $^1$H NMR (400 MHz, CDCl$_3$) δ 3.52(d, J=8.0 Hz, 1H), 3.38(s, 3H), 3.33(s, 3H), 3.31(d, J=8.0 Hz, 1H), 3.20(s, 2H), 2.48-2.40 (m, 2H), 2.20-2.01(m, 2H), 1.98-1.60(m, 8H), 1.58-1.10(m, 11H), 0.85(s, 3H).

Step 3. Preparation of compound B31. To a solution of ethyltriphenylphosphonium bromide (6.08 g, 16.4 mmol) in THF (30 mL), was added t-BuOK (1.84 g, 16.4 mmol). The reaction mixture was heated to 60° C. for 1 h and B30 (1.2 g, 3.29 mmol) was added to the mixture which was stirred at 60° C. for an additional 8 h. The reaction mixture was cooled, then diluted with H$_2$O (30 mL) and extracted with EtOAc (30 mL×2). The combined organic layer was washed with brine (20 mL), dried over Na$_2$SO$_4$ and concentrated. The residue was purified by silica gel column (PE: EtOAc=50:1 to 15:1) to afford product B31 (1.1 g, 88.7% yield) as yellow oil. $^1$H NMR (400 MHz, CDCl$_3$) δ 5.12-5.01(m, 1H), 3.54(d, J=8.0 Hz, 1H), 3.36(s, 3H), 3.32(s, 3H), 3.26(d, J=8.0 Hz, 1H), 3.18(s, 2H), 2.36-2.10 (m, 4H), 1.86-1.65(m, 2H), 1.52-1.01(m, 16H), 0.85(s, 3H).

Step 4. Preparation of compound B32. To a solution of B31 (1 g, 2.65 mmol) in THF (30 mL) was added dropwise a solution of BH$_3$-Me$_2$S (2.65 mL, 10 M) at 0° C. The solution was stirred at 25° C. for 4 h. TLC (PE:EtOAc=3:1) showed the reaction was almost complete. After cooling to 0° C., a solution of NaOH (10.6 mL, 3 M) was added very slowly. After the addition was complete, H$_2$O$_2$ (4.82 mL, 33%) was added slowly and the inner temperature was maintained below 10° C. The resulting solution was stirred at 25° C. for 2 h. The resulting solution was extract with EtOAc (20 mL×3). The combined organic solution was washed with saturated aqueous Na$_2$S$_2$O$_3$ (30 mL×3), brine (30 mL), dried over Na$_2$SO$_4$ and concentrated in vacuum to give the crude product (1.1 g) as yellow solid. The crude product was used for the next step without further purification.

Step 5. Preparation of compound 11. A mixture of B32 (1.0 g, 2.53 mmol), PCC (0.816 g, 3.79 mmol) and silica gel (0.897 g, =1/1.1) in DCM (15 mL) was stirred at 30° C. for 2 h, the reaction mixture color became brown. TLC (PE/EtOAc=3/1) showed the reaction was complete. The solution was filtered and the filter cake was washed with DCM (20 mL). The combined filtrate was concentrated in vacuum. The residue was purified by silica gel column eluted with PE/EtOAc=15/1 to 5/1 to give compound 11 (850 mg, 85.3%) as white solid. MS ESI calcd. for C$_{24}$H$_{41}$O$_4$[M+H]$^+$ 393, found 375([M+H−18]$^+$). $^1$H NMR (400 MHz, CDCl$_3$) δ 3.52(d, J=8.0 Hz, 1H), 3.40(s, 3H), 3.33(s, 3H), 3.28(d, J=8.0 Hz, 1H), 3.22(s, 2H), 2.53(t, J$_1$=16.0 Hz, J$_2$=8.0 Hz, 1H), 2.18-2.10(m, 5H), 2.05-1.95(m, 2H), 1.85-1.30(m, 11H), 1.20-1.01(m, 8H), 0.61(s, 3H).

Example 12. Preparation of 13

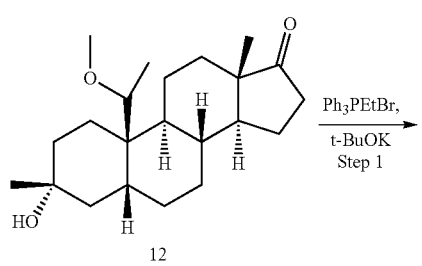

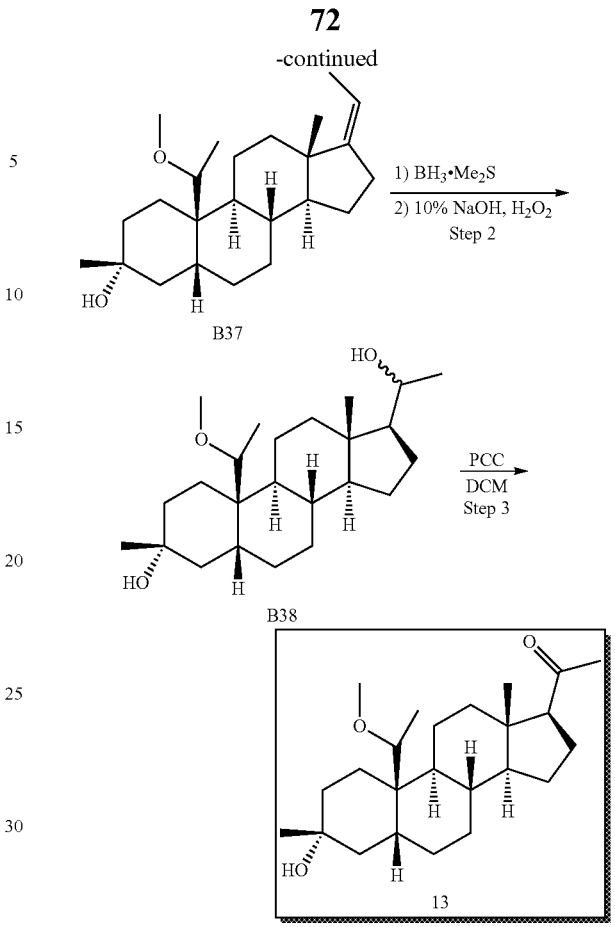

Step 1. Preparation of compound B37. To a solution of PPh$_3$EtBr (3.18 g, 8.58 mmol) in THF (15 mL) was added t-BuOK (962 mg, 8.58 mmol) at 25° C. After stirring at 60° C. for 1 h, a solution of 12 (1 g, 2.86 mmol) in THF (5 mL) was added drop wise at 60° C. Then the reaction mixture was stirred at 60° C. for 16 hrs. TLC (PE/EtOAc=5/1) showed the reaction was complete. The mixture was poured into ice-water (100 mL) and extracted with EA (50 mL*2). The organic layer was washed with brine (50 mL), dried over Na$_2$SO$_4$ and filtered, concentrated in vacuum. The residue was purified by silica gel column eluted with PE/EtOAc=15/1 to afford B37 (1 g, Purity: 80%, Yield: 77.6%) as a white solid. $^1$H NMR CDCl3 Bruker_P_400 MHz δ 5.18-4.99 (m, 1H), 3.83-3.71 (m, 1H), 3.30 (s, 3H), 2.45-2.09 (m, 3H), 2.01-1.81 (m, 3H), 1.68-1.58 (m, 6H), 1.58-1.37 (m, 10H), 1.31-1.12 (m, 14H), 1.08-1.03 (m, 3H), 0.91 (s, 3H).

Step 2. Preparation of compound B38. To a solution of B37 (1 g, 2.77 mmol) in THF (20 mL) was added drop wise a solution of BH$_3$-Me$_2$S (2.77 mL, 27.7 mmol) at 0° C. The solution was stirred at 25° C. for 16 hrs. TLC (PE/EtOAc=2/1) showed a new spot was obtained and a little material was remained. After cooling to 0° C., a solution of NaOH (9.23 mL, 3 M) was added very slowly. After the addition was complete, H$_2$O$_2$ (4.5 mL, 33%) was added slowly and the inner temperature was maintained below 10° C. The resulting solution was stirred at 25° C. for 2 hrs. TLC (PE/EtOAc=2/1) showed the reaction was complete. The resulting solution was extract with EtOAc (20 mL*2). The combined organic layer was washed with saturated aqueous Na$_2$S$_2$O$_3$ (50 mL×2), brine (50 mL), dried over Na$_2$SO$_4$, filtered and concentrated in vacuum to give B38 (0.9 g, crude) as a white solid. The crude product was used for the next step without further purification.

Step 3. Preparation of compound 13. To a solution of B38 (800 mg, 2.11 mmol) in DCM (10 mL) was added PCC (907 mg, 4.22 mol) at 25° C. The mixture was stirred at 25° C. for 2 hrs. TLC showed the reaction was complete. The solution was filtered and the filter cake was washed with DCM (50 mL*2). The combined filtrate was concentrated in vacuum. The residue was purified by silica gel column eluted with (PE/EtOAc=5/1) to afford 13 (600 mg, Purity: 90%, Yield: 68%) as a white solid. The 13 (100 mg, Purity: 90%) was purified by prep. HPLC (25° C.,column:DuraShell 150*25 mm*5 um, gradient: 48-78% B, 10 mM NH$_4$HCO$_3$-ACN), flow rate: 25 mL/min) to give 13 (10 mg, Purity: 100%, Yield: 10.0%) as white solid.

$^1$H NMR CDCl3 Bruker_P_400 MHz δ 3.78-3.74 (m, 1H), 3.27 (s, 3H), 2.56-2.51 (m, 1H), 2.22-2.16 (m, 1H), 2.12 (s, 3H), 2.06-1.94 (m, 2H), 1.91-1.79 (m, 1H), 1.74-1.61 (m, 6H), 1.50-1.32 (m, 6H), 1.29-1.10 (m, 10H), 1.09-1.02 (m, 3H), 0.64 (s, 3H)

LCMS Rt=1.067 min in 2.0 min chromatography, 30-90 AB, purity 100%, MS ESI calcd. For C$_{24}$H$_{40}$O$_3$[M+H−H$_2$O−MeOH]$^+$327, found 327.

Example 13. Preparation of 14

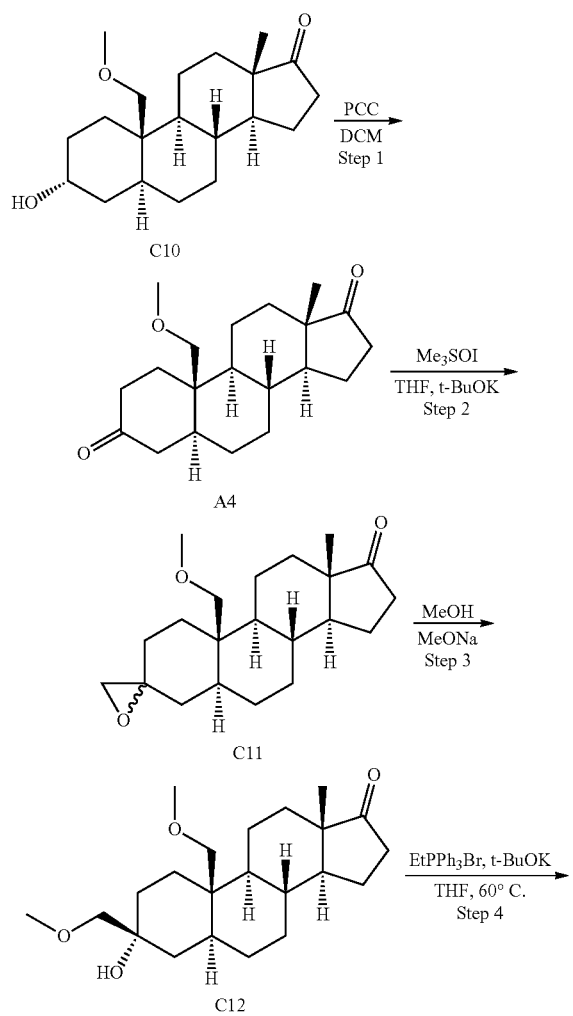

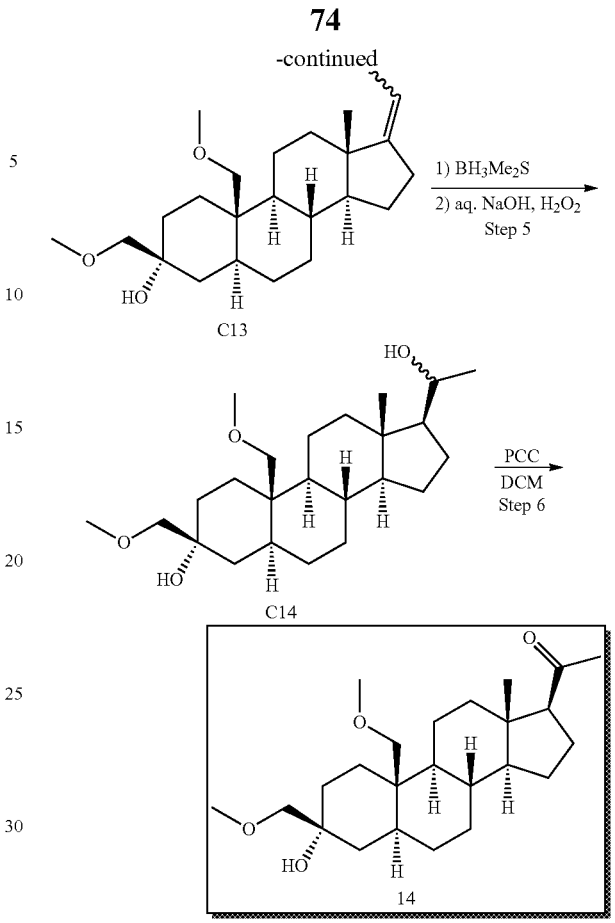

Step 1. Preparation of compound A4. To a solution of C10 (15.0 g, 46.81 mmol) in DCM (300 mL) was added PCC (15.1 g, 70.2 mmol), followed by silica gel (25 g). The reaction mixture was stirred at 25° C. for 3 hours. When TLC (stained with PMA) showed that the reaction completed, the reaction mixture was filtered through a pad of celite and the filtrate was concentrated under reduced pressure to afford crude product as brown oil, which was purified by column chromatography on silica gel (eluted with Petroleum ether/EtOAc=3:1) to afford desired product as yellow solid (15 g, 100% yield). $^1$H NMR (400 MHz, CDCl$_3$) δ 3.69-3.59 (m, 2H), 3.32 (s, 3H), 2.55-2.36 (m, 4H), 2.34-2.23 (m, 1H), 2.19-2.02 (m, 2H), 1.98-1.76 (m, 4H), 1.67-1.44 (m, 3H), 1.42-1.33 (m, 2H), 1.31-1.14 (m, 4H), 1.07-0.94 (m, 1H), 0.89 (s, 3H), 0.85-0.75 (m, 1H).

Step 2. Preparation of compound C11. To a suspension of Me$_3$SOI (4.13 g, 12.5 mmol, 1.5 eq) in THF (110 mL) was added tBuOK (2.8 g, 25.0 mmol, 2.0 eq). The reaction mixture was stirred at 25° C. for 1 hour. Then solution of A4 (4.0 g, 12.5 mmol, 1.0 eq) in THF (10 mL) was added to the reaction mixture and stirred for 5 hours. When TLC (Petroleum ether/EtOAc=3:1, stained with PMA) showed that the reaction completed, the reaction mixture was quenched with sat.aq. NH$_4$Cl (150 mL), extracted with EtOAc (100 mL*2). The combined organic layer was washed with brine (150 mL), dried over Na$_2$SO$_4$ and concentrated under reduced pressure to afford the desired product as colorless oil (4.0 g, crude), which was used in next step without further purification.

Step 3. Preparation of compound C12. To a solution of C11 (4.0 g, 12.1 mmol) in MeOH (150 mL) was added MeONa (1.95 g, 36.1 mmol). The reaction mixture was heated to 60° C. and stirred for 5 hours. When TLC showed that the reaction completed, the reaction mixture was concentrated under reduced pressure to remove most of the solvent. The residue was dissolved with EtOAc (200 mL), washed with $H_2O$ (100 mL) and brine (100 mL), dried over Na2SO4 and concentrated under reduced pressure to afford crude product as brown oil, which was purified by column chromatography on silica gel (eluted with Petroleum ether/EtOAc=3:1) to afford desired product as colorless oil (2.4 g, 55% yield, 2 Steps).

$^1$H NMR (400 MHz, CDCl$_3$) δ 3.49 (d, J=10.2 Hz, 1H), 3.41-3.34 (m, 4H), 3.29 (s, 3H), 3.20 (s, 2H), 2.43 (dd, J=19.2, 8.6 Hz, 1H), 2.13-1.88 (m, 4H), 1.83-1.67 (m, 5H), 1.55-1.33 (m, 5H), 1.27-1.12 (m, 6H), 1.08-0.97 (m, 1H), 0.91-0.80 (m, 4H).

Step 4. Preparation of compound C13. To a solution of CH$_3$CH$_2$PPh$_3$Br (7.31 g, 19.7 mmol, 3.0 eq) in THF (20 mL) was added tBuOK (2.21 g, 19.7 mmol, 3.0 eq) at 25° C., after addition, the reaction mixture was heated to 60° C. and stirred for 1 hour. Then C12 (2.4 g, 1.0 eq) was added and the reaction mixture was stirred at this temperature for 16 hours. When TLC showed that the reaction completed, the reaction mixture was poured into H$_2$O (50 mL), extracted with EtOAc (50 mL*2). The combined organic layer was washed with brine (50 mL), dried over Na$_2$SO$_4$ and concentrated under reduced pressure to afford crude product as brown oil, which was purified by column chromatography on silica gel (eluted with Petroleum ether/EtOAc=10:1) to afford desired product C13 as colorless oil(1.67 g, 80.2%).

$^1$H NMR (400 MHz, CDCl$_3$) δ 5.07-5.14 (m, 1H), 3.48 (d, J=10.0 Hz, 1H), 3.41-3.35 (m, 4H), 3.29 (s, 3H), 3.20 (s, 2H), 2.41-2.08 (m, 3H), 1.99-2.02 (m, 1H), 1.78-1.57 (m, 9H), 1.55-1.30 (m, 6H), 0.73-1.22 (m, 10H).

Step 5. Preparation of compound C14. Borane-tetrahydrofuran complex (15.3 mL, 15.3 mmol, 1.0 M solution in THF) was added to a solution of C13 (1.67 g, 4.43 mmol) in anhydrous tetrahydrofuran (20 mL) at room temperature under nitrogen, after which the mixture was stirred for 1 h. The mixture was cooled in an ice bath and 10% aqueous sodium hydroxide solution (8.8 mL) was added, followed by 30% aqueous hydrogen peroxide solution (8.8 mL). The resulting mixture was stirred at room temperature for 1 h and then extracted with ethyl acetate (3×50 mL). The combined organic extracts were washed sequentially with 10% aqueous sodium sulfite and saturated aqueous sodium chloride solutions, dried with sodium sulfate and filtered. The solvents were removed under reduced pressure to provide crude C14 as a colorless oil that was used in the next step without further purification (1.77 g, crude).

Step 6. Preparation of compound 14. To a solution of C14 (1.77 g, 4.48 mmol) in CH$_2$Cl$_2$ (20 mL) was added silica gel (2.55 g). Then the PCC (1.44 g, 6.72 mmol) was added. The mixture was stirred at 25° C. for 16 hours. TLC showed the reaction was completed. The mixture was filtered. The solution was extracted with EtOAc (20 mL*3) and dried over Na2SO4The combined organic layer was concentrated under vacuum and purified by column chromatography on silica gel (PE:EA=10:1) to give 14 (1.5 g) as a white solid.

$^1$H NMR (400 MHz, CDCl$_3$) δ3.46 (d, J=10.0 Hz, 1H), 3.41-3.34 (m, 4H), 3.28 (s, 3H), 3.20 (s, 2H), 2.53 (t, J=8.9 Hz, 1H), 2.22-1.94 (m, 7H), 1.75-1.61 (m, 5H), 1.55-0.80 (m, 14H), 0.62 (s, 3H). LCMS $t_R$=1.978 min in 2 min chromatography, 10-80AB_E, purity 100%, MS ESI calcd. for C$_{24}$H$_{40}$O$_4$[M+H−H$_2$O−2MeOH]$^+$311, found 311.

Assay Methods

Compounds provided herein can be evaluated using various assays; examples of which are described below.

Steroid Inhibition of TBPS Binding

[35S]-Butylbicyclophosphorothionate (TBPS) binding assays using rat brain cortical membranes in the presence of 5 μM GABA has been described (Gee et al, J. Pharmacol. Exp. Ther. 1987, 241, 346-353; Hawkinson et al, Mol. Pharmacol. 1994, 46, 977-985; Lewin, A. H et al., Mol. Pharmacol. 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

Patch Clamp Electrophysiology of Recombinant α$_1$β$_2$γ$_2$ and α$_4$β$_3$δ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA EC$_{20}$=2 μM). LTK cells are stably transfected with the α$_1$β$_2$γ$_2$ subunits of the GABA receptor and CHO cells are transiently transfected with the α$_4$β$_3$δ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., Science, 1988, 242, 1306-1308). Because responses in distant cells are not adequately voltage clamped and because of uncertainties about the extent of coupling (Verdoorn et al., Neuron 1990, 4, 919-928), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, $CaCl_2$ 1.8 mM, $MgCl_2$ 1 mM, HEPES 10 mM, D-Glucose 10 mM, pH (NaOH) 7.4. In some cases 0.005% cremophor was also added. Intracellular (pipette) solution contained: KCl 130 mM, $MgCl_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (1 ml/min) with bath solution. After formation of a Gigaohm seal between the patch electrodes and the cell (pipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 µM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 µM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100.

TABLE 1

TBPS binding of the exemplary compounds.

| Name | TBPS $IC_{50}$ (nM) |
|---|---|
| 1 | C |
| 2 | C |
| 3 | B |
| 4 | A |
| 5 | A |
| 6 | B |
| 7 | E |
| 8 | E |
| 9 | D |
| 10 | C |

For Table 1: TBPS: "A" indicates an $IC_{50}$<10 nM, "B" indicates an $IC_{50}$ 10 to <50 nM, "C" indicates an $IC_{50}$ 50 nM to <100 nM, "D" indicates an $IC_{50}$ 100 nM to <500 nM, and "E" indicates $IC_{50}$ greater than or equal to 500 nM.

TABLE 2

Electrophysiological evaluation of the exemplary compounds at $GABA_A$-R.

| Name | GABA (α1β2γ2) Qpatch in Ltk, % efficacy at 10 µM | GABA (α4β3δ) Manual patch in CHO, % efficacy at 10 µM |
|---|---|---|
| 1 | B | C |
| 2 | C | D |
| 5 | C | C |
| 6 | B | D |

For Table 2. GABAA receptors α1β2γ2 and α4β3δ % efficacy: "A" 10-100, "B">100-500, "C">500; D indicates the data is not available or has not been determined.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method for treating a CNS-related disorder selected from the group consisting of tremor, a bipolar disorder, a major depressive disorder (MDD), or an anxiety disorder, in a human subject in need thereof comprising administering to the human subject a therapeutically effective amount of a) a compound of Formula (I) or a pharmaceutically acceptable salt thereof or b) a pharmaceutical composition comprising a compound of Formula (I) or a pharmaceutically acceptable salt thereof and a pharmaceutically acceptable excipient, wherein:

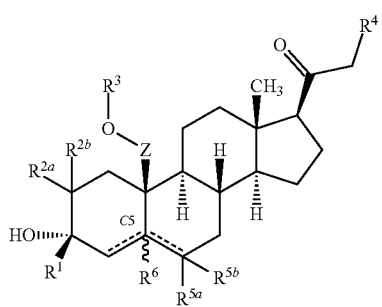

Formula (I)

$R^1$ is $C_1$-$C_6$ alkyl, $C_2$-$C_6$ alkenyl, $C_2$-$C_6$ alkynyl, carbocyclyl, or heterocyclyl;

each of $R^{2a}$ and $R^{2b}$ is independently hydrogen, $C_1$-$C_6$ alkyl, halo, cyano, —$OR^A$, or —$NR^B R^C$, $R^{2a}$ and $R^{2b}$ together with the carbon atom to which they are attached form a ring;

$R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, or —$C(O)NR^B R^C$;

$R^4$ is hydrogen, $C_1$-$C_6$ alkyl, $C_2$-$C_6$ alkenyl, $C_2$-$C_6$ alkynyl, carbocyclyl, or —$OR^A$;

==== represents a single or double bond, wherein when one ==== is a double bond, the other ==== is a single bond;

wherein when the ==== between —$CR^6$ and —$CR^{5a}R^{5b}$ is a double bond, then one of $R^{5a}$ or $R^{5b}$ is absent; and when one of the ==== is a double bond, $R^6$ is absent;

each of $R^{5a}$ and $R^{5b}$ is independently absent, hydrogen, $C_1$-$C_6$ alkyl, or halo;

$R^6$ is absent or hydrogen;

Z is —$CR^{7a}R^{7b}$—, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring;

$R^A$ is hydrogen, $C_1$-$C_6$ alkyl, carbocyclyl, heterocyclyl, aryl, or heteroaryl; and each of $R^B$ and $R^C$ is independently hydrogen, $C_1$-$C_6$ alkyl, carbocyclyl, heterocyclyl, aryl, heteroaryl, or taken together with the atom to which they are attached form a ring.

2. The method of claim 1, wherein $R^1$ is methyl.

3. The method of claim 1, wherein both $R^{2a}$ and $R^{2b}$ are hydrogen.

4. The method of claim 1, wherein $R^3$ is $C_2$-$C_6$ alkyl, $C_2$-$C_6$ alkenyl, $C_2$-$C_6$ alkynyl, carbocyclyl, heterocyclyl, $C(O)R^A$, —$C(O)OR^A$, or —$C(O)NR^B R^C$.

5. The method of claim 4, wherein $R^3$ is —$C(O)NR^B R^C$.

6. The method of claim 1, wherein $R^4$ is hydrogen, $C_1$-$C_6$ alkyl, or —OH.

7. The method of claim 6, wherein $R^4$ is hydrogen.

8. The method of claim 1, wherein both $R^{2a}$ and $R^{2b}$ are hydrogen, the ==== between —$CR^6$ and —$CR^{5a}R^{5b}$ is a single bond, and both $R^{5a}$ and $R^{5b}$ are hydrogen.

9. The method of claim 1, wherein Z is —$CH_2$—.

10. The method of claim 1, wherein $R^{7a}$ is hydrogen and $R^{7b}$ is $C_1$-$C_6$ alkyl.

11. The method of claim 1, wherein the compound of Formula (I) is a compound of Formula (Ia):

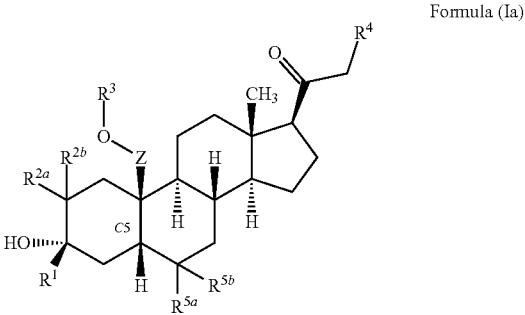

Formula (Ia)

or a pharmaceutically acceptable salt thereof, wherein:

$R^1$ is $C_1$-$C_6$ alkyl, $C_2$-$C_6$ alkenyl, $C_2$-$C_6$ alkynyl, carbocyclyl, or heterocyclyl;

each of $R^{2a}$ and $R^{2b}$ is independently hydrogen, $C_1$-$C_6$ alkyl, halo, cyano, —$OR^A$, or —$NR^B R^C$, or $R^{2a}$ and $R^{2b}$ together with the carbon atom to which they are attached form a ring;

$R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —$C(O)R^A$, —$C(O)OR^A$, or —$C(O)NR^B R^C$;

$R^4$ is hydrogen, $C_1$-$C_6$ alkyl, $C_2$-$C_6$ alkenyl, $C_2$-$C_6$ alkynyl, carbocyclyl, or $OR^A$;

each of $R^{5a}$ and $R^{5b}$ is independently hydrogen, $C_1$-$C_6$ alkyl, or halo;

Z is —$CR^{7a}R^{7b}$—, wherein each of $R^{7a}$ and $R^{7b}$ is independently hydrogen or $C_1$-$C_6$ alkyl, or $R^{7a}$ and $R^{7b}$, together with the carbon atom to which they are attached, form a ring;

$R^A$ is hydrogen, $C_1$-$C_6$ alkyl, carbocyclyl, heterocyclyl, aryl, or heteroaryl; and each of $R^B$ and $R^C$ is independently hydrogen, $C_1$-$C_6$ alkyl, carbocyclyl, heterocyclyl, aryl, heteroaryl, or taken together with the atom to which they are attached form a ring.

12. The method of claim 11, wherein $R^1$ is methyl.

13. The method of claim 11, wherein $R^3$ is $C_2$-$C_6$ alkyl, $C_2$-$C_6$ alkenyl, $C_2$-$C_6$ alkynyl, carbocyclyl, heterocyclyl, —$C(O)R^A$, —$C(O)OR^A$, or —$C(O)NR^B R^C$.

14. The method of claim 11, wherein $R^3$ is $C_1$-$C_6$ alkyl.

15. The method of claim 11, wherein $R^4$ is hydrogen.

16. The method of claim 11, wherein both $R^{2a}$ and $R^{2b}$ are hydrogen and both $R^{5a}$ and $R^{5b}$ are hydrogen.

17. The method of claim 11, wherein the compound of Formula (Ia) is selected from a group consisting of:

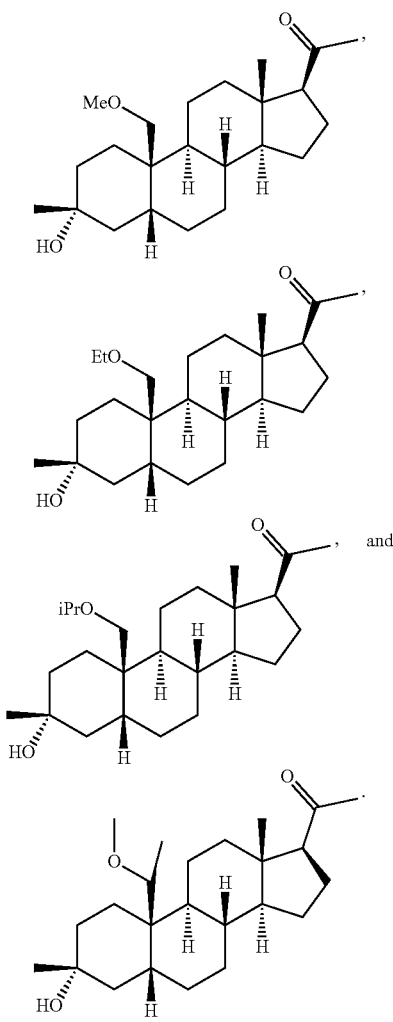

18. The method of claim 1, wherein the compound of Formula (I) is a compound of Formula (Ib):

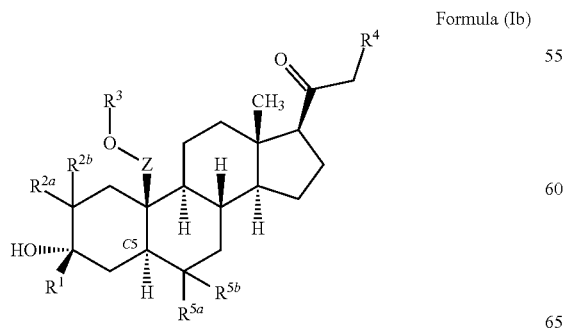

Formula (Ib)

or a pharmaceutically acceptable salt thereof, wherein:

$R^1$ is $C_1$-$C_6$ alkyl, $C_2$-$C_6$ alkenyl, $C_2$-$C_6$ alkynyl, carbocyclyl, or heterocyclyl;

each of $R^{2a}$ and $R^{2b}$ is independently hydrogen, $C_1$-$C_6$ alkyl, halo, cyano, —$OR^A$, or —$NR^BR^C$, or $R^{2a}$ and $R^{2b}$ together with the carbon atom to which they are attached form a ring;

$R^3$ is hydrogen, $C_1$-$C_6$ alkyl, $C_2$-$C_6$ alkenyl, $C_2$-$C_6$ alkynyl, carbocyclyl, heterocyclyl, aryl, heteroaryl, —C(O)$R^A$, —C(O)O$R^A$, or —C(O)N$R^BR^C$;

$R^4$ is hydrogen, $C_1$-$C_6$ alkyl, $C_2$-$C_6$ alkenyl, $C_2$-$C_6$ alkynyl, carbocyclyl, or $OR^A$;

each of $R^{5a}$ and $R^{5b}$ is independently hydrogen, $C_1$-$C_6$ alkyl, or halo;

Z is —$CR^{7a}R^{7b}$—, wherein each of $R^1$ and $R^{7b}$ is independently hydrogen or $C_1$-$C_6$ alkyl, or $R^{7a}$ and $R^{7b}$, together with the carbon atom to which they are attached, form a ring;

$R^A$ is hydrogen, $C_1$-$C_6$ alkyl, carbocyclyl, heterocyclyl, aryl, or heteroaryl; and each of $R^B$ and $R^C$ is independently hydrogen, $C_1$-$C_6$ alkyl, carbocyclyl, heterocyclyl, aryl, heteroaryl, or taken together with the atom to which they are attached form a ring.

19. The method of claim 18, wherein $R^1$ is methyl.

20. The method of claim 18, wherein $R^3$ is $C_2$-$C_6$ alkyl, $C_2$-$C_6$ alkenyl, $C_2$-$C_6$ alkynyl, carbocyclyl, heterocyclyl, —C(O)$R^A$, —C(O)O$R^A$, or —C(O)N$R^BR^C$.

21. The method of claim 18, wherein $R^3$ is $C_1$-$C_6$ alkyl.

22. The method of claim 20, wherein $R^3$ is —C(O)N$R^BR^C$.

23. The method of claim 18, wherein $R^4$ is —OH.

24. The method of claim 18, wherein $R^4$ is hydrogen.

25. The method of claim 18, wherein both $R^{2a}$ and $R^{2b}$ are hydrogen and both $R^{5a}$ and $R^{5b}$ are hydrogen.

26. The method of claim 18, wherein the compound of Formula (Ib) is selected from a group consisting of:

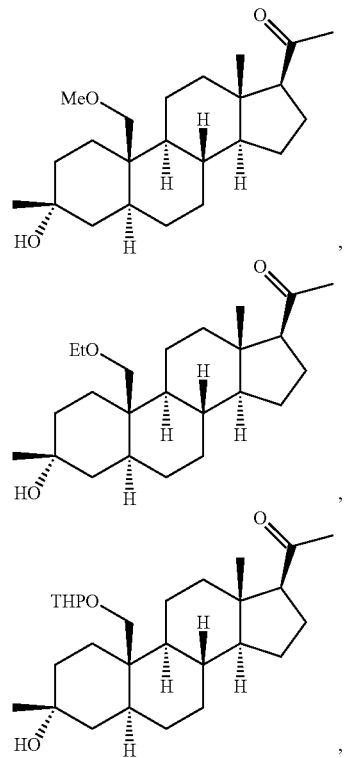

-continued

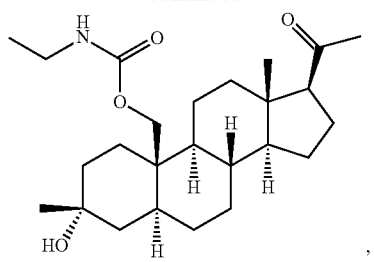
,

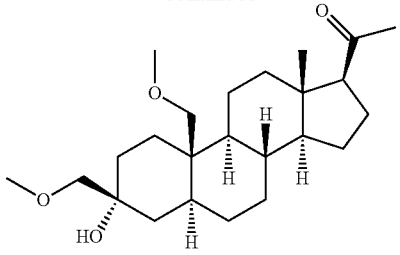
.

27. The method of claim 1, wherein the CNS-related disorder is a major depressive disorder.

28. The method of claim 1, wherein the CNS-related disorder is tremor.

29. The method of claim 28, wherein the tremor is essential tremor.

30. The method of claim 1, wherein the CNS-related disorder is a bipolar disorder.

31. The method of claim 1, wherein the CNS-related disorder is an anxiety disorder.

32. The method of claim 31, wherein the anxiety disorder is a generalized anxiety disorder (GAD).

33. The method of claim 31, wherein the anxiety disorder is a social anxiety disorder.

* * * * *